US007632680B2

(12) United States Patent
Neuman et al.

(10) Patent No.: US 7,632,680 B2
(45) Date of Patent: Dec. 15, 2009

(54) COMPOSITIONS AND METHODS FOR ISOLATION, PROPAGATION, AND DIFFERENTIATION OF HUMAN STEM CELLS AND USES THEREOF

(75) Inventors: Toomas Neuman, Santa Monica, CA (US); Michel Levesque, Beverly Hills, CA (US)

(73) Assignee: Levesque Biosciences, Inc., Beverly Hills, CA (US)

( * ) Notice: Subject to any disclaimer, the term of this patent is extended or adjusted under 35 U.S.C. 154(b) by 503 days.

(21) Appl. No.: 10/216,677

(22) Filed: Aug. 8, 2002

(65) Prior Publication Data

US 2003/0118566 A1 Jun. 26, 2003

Related U.S. Application Data

(60) Provisional application No. 60/310,727, filed on Aug. 8, 2001, provisional application No. 60/312,714, filed on Aug. 16, 2001.

(51) Int. Cl.
*C12N 5/08* (2006.01)
*A61K 35/30* (2006.01)

(52) U.S. Cl. .................. 435/387; 424/93.7; 424/570

(58) Field of Classification Search ........................ None
See application file for complete search history.

(56) References Cited

U.S. PATENT DOCUMENTS

| | | | | |
|---|---|---|---|---|
| 5,411,883 A | * | 5/1995 | Boss et al. | ..................... 435/29 |
| 5,750,376 A | * | 5/1998 | Weiss et al. | ............... 435/69.52 |
| 5,753,506 A | | 5/1998 | Johe | |
| 5,851,832 A | * | 12/1998 | Weiss et al. | .................. 435/368 |
| 5,968,829 A | * | 10/1999 | Carpenter | .................... 435/467 |
| 5,981,165 A | | 11/1999 | Weiss et al. | |
| 6,071,889 A | | 6/2000 | Weiss | |
| 6,090,622 A | * | 7/2000 | Gearhart et al. | ............. 435/366 |
| 6,277,820 B1 | * | 8/2001 | Rosenthal et al. | ............. 514/12 |

FOREIGN PATENT DOCUMENTS

| WO | WO 91/09936 | 7/1991 |
|---|---|---|
| WO | WO 00/58451 | 10/2000 |

OTHER PUBLICATIONS

Vickers et al. 2002. Drugs Aging 19:487-494.*
Kandel 1993. Principles of Neural Science, p. 290, 976-980.*
Sweeney 1989, abstract of PhD Dissertation entitled "Embryonal carcinoma stem cell differentiation: Influence of retinoic acid and cell/extracellular matrix interactions".*
Schneider 1999. Journal of Pharmacology and Experimental Therapeutics 290:731-739.*
Defer 1996. Brain 119:41-50.*
Baetge 1993. Annals of the New York Academy of Sciences 695:285-291.*
Mehta 1998 J. Neurosurg 88:1088-1095.*
Olanow 1996 Trends Neurosci 19:102-109.*
Palm et al., "Effects of growth factors on the developmental potential of human CNS-derived neurospheres" Society for Neuroscience Abstracts, vol. 26 , p. 1 (Nov. 2000).
Svendsen et al., "Increased survival of rat EGF-generated CNS precursor cells using B27 supplemented medium," Exp Brain Res (1995) 102, pp. 407-414.
Kopyov et al. 1989. "Grafting of the embryonic brain tissue helps the survival of rats after severe craniocerebral trauma." Abstract, The 3rd International Symposium on Neural Transplantation, U.K., p. 139.
Markham C.M.et al. 1994. "Transplantation of fetal mesencephalic tissue in Parkinson's patients." Stereotactic and Functional Neurosurgery, vol. 62: p. 134-140.
Palmer, T. et al. 1997. "The adult rat hippocampus contains primordial neural stem cells." Molecular and Cellular Neuroscience. vol. 8: p. 389-404.
Spencer D.O. et al. 1992. "Unilateral transplantation of human fetal mesencephalic tissue into the caudate nucleus of patients with Parkinson's disease." The New England Journal of Medicine, vol. 327: p. 1541-1548.
Suhonen, J.O. et al. 1996. "Differentiation of adult hippocampus-derived progenitors into olfactory neurons in vivo." Nature vol. 383: p. 624-627.
Vescovi, A.L. et al. 1997. "Continuous generation of human catecholaminergic neurons by embryonic CNS stem cells." vol. 23 (I). In 27th Meeting Soc. Neurosci.: New Orleans, Lousiana, Oct. 25-30, Abs. 131.6, p. 319.
Bankiewicz et al. 1991. Fetal nondopaminergic neural implants in parkinsonian primates. Journal of Neurosurgery, 74: 97-104.
Backlund et al. 1987. Journal American Medical Association 258:1891.
Backlund et al. 1989. British Journal Neurosurgery 3(6); 627-629.
Backlund et al. 1987. Toward a transplantation therapy in Parkinson's disease. A progress report from continuing clinical experiments. Ann NY Acad Sci: 495: 658-73.
Backlund et al. Feb. 1985. Transplatation of adrenal medullary tissue to striatum in parkinsonism. First clinical trials. Journal of Neurosurgery. 62(2): 169-73.
Brundin et al. 1991. Intracerebral grafting of dopamine neurons: Experimental basis for clinical trials in patients with Parkinson's disease. Annals of the New York Academy of Sciences, V: 473-495.
Carpenter et al. 1999. In Vitro Expansion of a Multipotent Population of Human Neural Progenitor Cells. Experimintal Neurology. 158: 256-278.
Chalmers-Redman, R.M.E., Priestley, T., Kemp, J. A., Fine, A. 1997. In vitro propagation and inducible differentiation of multipotent progenitor cells from human fetal brain. Neurosc., 76, 1121-1128.
Chen L. et al. 1991. Cellular replacement therapy for neurologic disorders: Potential of genetically engineered sells. Journal of Cellular Biochemistry, 45; 252-257.
Davis, A.A. and Temple, S. 1994. A self-renewing multipotential stem cell in embryonic rat cerebral cortex. Nature, 372:263-266.

(Continued)

*Primary Examiner*—Daniel E. Kolker
(74) *Attorney, Agent, or Firm*—Knobbe Martens Olson & Bear LLP

(57) ABSTRACT

The invention is directed to the field of human stem cells and includes methods and compositions for isolating, propagating, and differentiating human stem cells. The invention provides therapeutic uses of the methods and compositions, including autologous transplantation of treated cells into humans for treatment of Parkinson's and other neuronal disorders.

25 Claims, No Drawings

OTHER PUBLICATIONS

Diamond S.G., Markham C.H., Rand,R.W., Becker, D.P., Treciokas, L.J. 1994: Four-year follow-up of adrenal-to—brain transplants in Parkinson's disease. Archives of Neurology, 51 559-563.

Espejo, E.F., Montoro, R.J., Armengol, J.A., López-Barneo, J. 1998. Cellular and functional recovery of Parkinsonian rats after intrastriatal transplantation of carotid body cell aggregates. Neuron, 20: 197-206.

Freed et al. 1989. Therapeutic effects of human fetal dopamine cells transplanted in a patient with Parkinson's disease. In S.B. Dunnet and S.R. Richards, eds. Neural Transplantation: From Molecular Basis to Clinical Application. Amsterdam: Elsevier Science Publishers, 1989.

Freed C.R., Breeze R.E., Rosenberg N.L., Schneck S.A., Kriek E., Qi J., et al. 1992. Survival of implanted fetal dopamine cells and neurologic improvement 12 to 46 months after transplantation for Parkinson's disease. New England Journal of Medicine, 327: 1549-1555.

Freeman, T and Olanow, 1991. Fetal homotransplants in the treatment of Parkinson's disease. Archives of Neurology, 48: 900-901.

Fricker, R.A., Carpenter, M.K., Winkler, C., Greco, C., Gates, M.A. and Bjorklund, A. 1999. Site-specific migration and neuronal differentiation of human neural progenitor cells after transplantation in the adult rat brain. J. Neurosci. 19: 5990-6005.

Gage and Fisher, 1991. Intracerebral grafting: A tool for the neurologist. Neuron, 6: 1-12.

Goetz et al. 1989. Multicenter study of autologous adrenal medullary transplantation to the corpus striatum in patients with advanced Parkinson's disease. New England Journal of Medicine, 320: 337-341.

Gritti et al. 1999. Epidermal and Fibroblast Growth Factors Behave as Mitogenic Regulators for a Single Multipotent Stem Cell-Like Population from the Subventricular Region of the Adult Mouse Forebrain. The Journal of Neuroscience, 19(9): 3287-3297.

Gritti et al., 1996. Multipotential stem cells from the adult mouse brain proliferate and self- renew in response to basic fibroblast growth factor. J. Neurosci. 16: 1091-1100.

Hajihosseini et al. 1999. A Subset of Fibroblast Growth Factors (Fgts) Promote Survival, but Fgf-8b Specifically Promotes Astroglial Differentiation of Rat Cortical Precursor Cells. Molecular and Cellular Neuroscience. 14: 468-485.

Hitchcock et al. 1989. Stereotactic implantation of foetal mesencephalon (STIM): The U.K. experience. In S.B. Dunnet and S.R. Richards, eds. Neural Transplantation: From Molecular Basis to Clinical Application. Amsterdam: Elsevier Science Publishers.

Lang, A.E., Lozano, A.M. 1998. Parkinson's disease. New England Medicine, 1130-1143.

Langston, W, et al, 1992: Core Assessment Program for Intracerebral Transplantation. Movement Disorders, vol. 7: 2-13.

Leigh K., Elisevich K., Rogers K.A. 1994. Vascularization and microvascular permeability in solid versus cell suspension embryonic neural cells. Journal of Neurosurgery, 81:272-283.

Lendahl, V., Zimmerman, L.B. and McKay, R.D.G., (1990) CNS stem cells express a new class of intermediate filament protein., *Cell*, 60:585-595.

Lindvall O.: Transplants in Parkinson's disease. 1991. European Neurology, 31(Supp. 1): 17-27.

Lindvall, O., 1997. Neural transplantation: a hope for patients with Parkinson's disease. NeuroReport, 8, iii-x.

Lindvall. O. et al. Oct. 1987. Transplantation in Parkinson's disease: two cases of adrenal medullary grafts to the putamen. Ann Neurol. 22(4): 457-68.

Lois, C., Alvarez-Buylla, A. 1993. Proliferating subventricular zone cells in the adult mammalian forebrain can differentiate into neurons and glia. Proc. Natl. Acad. Sci. USA, 90:2074-2077.

Madrazo I., Drucker-Colin R., Diaz V., Martinez-Mata J., Torres C., Becerril J.J. 1987. Open microsurgical autograft of adrenal medulla to the right caudate nucleus in two patients with intractable Parkinson's disease. New England Journal of Medicine, 316:831-834.

Neuman, Toomas. Dec. 2000. Preclinical Trials on Parkinsonism. Spinal Cord Society. 3-10.

Neuman, Toomas. Aug. 2000. Cell Therapy of Human Spinal Cord injury. Spinal Cord Society. 6-9.

Olanow, C.W., Kordower, J.H., Freeman, T.B. 1996. Fetal nigral transplantation as a therapy for Parkinsons disease. Trends NeuTosci. 19: 102-109.

Olson et al. 1991. Arch. Neurol. 48:373-381.

Olson et al. 1985. Transplantation of monoamine-producing cell systems in oculo and intracranially: experiments in search of a treatment for Parkinson's Disease. Ann NY Acad Sci. 457: 105-26.

Palm, K, Salin-Nordstrom, T. Levesque, MF and Neuman T: Fetal and adult human CNS stem cells have similar molecular characteristics and developmental potential.Brain Res Mol Brain Res. May 31, 2000;78(1-2):192-5.

Reynolds, B.A., Weiss, S. 1992. Generation of neurons and astrocytes from isolated cells of the adult mammalian central nervous system. Science, 255: 1707-1710.

Rosenthal, A. 1998. Auto transplants for Parkinson's disease? Neuron, 20:169-172.

Sakakibara, 5., Imai, T., Hamaguchi, K., Okabe, M., Aruga, J., Nakajima, K., Yasutomi, D., Nagata, T., Kurihara, Y., Uesugi, 5., Miyata, T., Ogawa, M., Mikoshiba, K. and Okano, H. 1996 Mouse-Musashi-1, a neural RNA-binding protein highly enriched in the mammalian CNS stem cell., *Dev. Bioi.*, 176:230-242.

Schierle, G.S., Hansson, O., Leist, M., Nicotera, P., Widner, H., Brundin, P. 1999. Caspase inhibition reduces apoptosis and increases survival of nigral transplants. Nat Med, 5: 97-100.

Shamim et al. 1999. Sequential roles for Fgf4, En1 and Fgf8 in specification and regionalisation of the midbrain. Development 126: 945-959.

Sinclair, S.R., Svendsen, C.N., Torres, E.M., Fawsett, I.W., Dunnett, S.B. 1996. The effects of glial cell line-derived neurotrophic factor (GDNF) on embryonic nigra 1 grafts. NeuroReport, 7:2547-2552.

Svendsen, C.N., Clarke, D.J., Rosser, A.E., Dunnett, S.B. 1996. Survival and differentiation of rat and human epidermal growthfactor-responsive precursor cells following grafting into the lesioned adult central nervous system. Exp. Neurol., 137, 376-388.

Vescovi, A.L., Parati, E.A., Gritti, A., Poulin, P., Ferrario, M., Wanke, E., Frolichsthal-Schoeller, P., Cova, L., Arcellana-Panililio, M., Colombo, A. and Galli, R. 1999. Isolation and cloning of multipotential stem cells from the embryonic human CNS and establishment of transplantable human neural stem cell lines by epigenetic stimulation. Exp. Neurol. 156, 71-83.

Zawada, W.M., Zastrow, D.J., Clarkson, E.D., Adams, F.S., Bell, K.P., Freed, C.R. 1998. Growth factors improve immediate survival of embryonic dopamine neurons after transplantation into rats. Brain Res., 786 (1-2): 96-103.

Takahashi et al., "Retinoic acid and neurotrophins collaborate to regulate neurogenesis in adult-derived neural stem cell cultures," J. Neurobiol., 1999, vol. 38, pp. 65-81.

Levesque et al. "Therapeutic Microinjection of Autologous Adult Human Neural Stem Cells and Differentiated Neurons for Parkinson's Disease: Five-Year Post-Operative Outcome" The Open Stem Cell Journal, 2009, 1, 20-29.

Carlson et al. Brain implantation of engineered GAB-releasing cells suppress tremor in an animal model of Parkinsonism. Neuroscience, 2003: 119(4): 927-932.

Nyberg et al., 1987. Dopaminergic deficiency is more pronounced in putamen than in nucleus caudatus in Parkinson's disease. Neurochem. Pathos., 1: 193-202.

Winkler et al. Intranigral transplants of GABA-rich striatal tissue induce behavioral recovery in the rat Parkinson model and promote the effects obtained by intrastriatal dopaminergic transplants. Exp Neurol. Feb. 1999; 155(2): 165-186.

Winkler et al. Transplantation in the rat model of Parkinson's disease: ectopic versus homotopic graft placement. Prog Brain Res. 2000; 127: 233-265.

* cited by examiner

COMPOSITIONS AND METHODS FOR ISOLATION, PROPAGATION, AND DIFFERENTIATION OF HUMAN STEM CELLS AND USES THEREOF

RELATED APPLICATIONS

The present application claims priority under 35 U.S.C. §119(e) to U.S. Provisional Application Nos. 60/310,727 filed Aug. 8, 2001 and 60/312,714 filed Aug. 16, 2001.

FIELD OF THE INVENTION

The invention is directed to the field of human stem cells and includes methods and compositions for isolating, propagating, and differentiating human stem cells. The invention includes therapeutic uses of the methods and compositions, including autologous transplantation of treated cells into humans for treatment of Parkinson's and other diseases.

BACKGROUND OF THE INVENTION

Fetal tissue has been transplanted into human patients to treat Parkinsonism and other neurodegenerative diseases and is a promising treatment for many other conditions, including neurotrauma and injuries to the spinal cord. Fetal cells are very useful because they are multipotent, meaning that they have the potential to turn into many different kinds of specialized cells, for example a neuron (a brain cell) or a liver cell. A multipotent cell is sometimes called a stem cell. A cell that changes from a multipotent state into a specialized cell is said to differentiate into a differentiated (i.e., specialized) cell. Once a cell differentiates into a specialized cell it does not naturally return to a multipotent state. Thus, any cell that is not yet fully committed to a particular specialized cell type is referred to hereinafter as a "stem cell."

Transplantation of fetal tissue has had limited success. One technical limitation is that implanted fetal cells do not necessarily differentiate into the desired cell type. For example, a fetal cell put into the brain of a Parkinson's patient does not necessarily become a type of neuron that benefits the patient, such as a dopaminergic neuron. In addition, significant moral, ethical, and technological issues make a non-fetal source of cells desirable.

Scientists have learned that stem cells exist in mammals at all stages of development, including the adult stage. Adult stem cells are more specialized than fetal stem cells but have the natural potential to become one of a wide variety of cell types. The stem cell types are commonly named according to the tissue where they reside: for example, bone marrow stem cells, epidermal (skin) stem cells, or central nervous system stem cells. Many hospitals routinely capture bone marrow stem cells from patients undergoing chemotherapy. The cells are preserved outside of the body during treatment and subsequently implanted following treatment.

A substantial body of literature describes therapies based on introducing cells into patients. These therapies include treatments of Alzheimer's disease and Parkinson's disease. Such therapies are described, for example, in "Survival and differentiation of adult neuronal progenitor cells transplanted to the adult brain" by F. H. Gage et al., Proceedings of the National Academy of Science U.S.A. 92:11879-83 (1995); "Site-specific migration and neuronal differentiation of human neural progenitor cells after transplantation in the adult rat brain" by R. A. Fricker et al., Journal of Neuroscience, 19:5990-6005 (1999); and "Self-repair in the brain" by A. Bjorklund and O. Lindvall, Nature 405:892-3,895 (2000).

Parkinson's Disease and Intracerebral Transplantation

Parkinson's disease is a neurodegenerative disease characterized by profound loss of dopaminergic neurons in the substantia nigra. The loss of dopaminergic neurons in the substantia nigra results in the degeneration of the nigrostriatal dopamine system that regulates motor function. This, in turn, leads to motor dysfunction, consisting of poverty and slowness of voluntary movements, tremor, stooped posture, rigidity, and gait disturbance. There has been no cure for Parkinson's disease.

Modern knowledge of the pathogenesis of Parkinson's disease indicates that successful functional restoration can be achieved by replacing the lost dopamine in the damaged area of the brain. This understanding inspired attempts to replace dopamine by grafting dopamine producing cells, for example, fetal tissue rich in dopaminergic neurons, cells from the adrenal medulla, or dopaminergic neurons from another species, such as pigs, to the degenerated striatum. The ability of intracerebral grafts to induce behavioral recovery in brain-damaged recipients rests on the multitude of trophic, neurohumoral, and synaptic mechanisms that may allow the implanted tissue to promote host brain function and repair. To what extent intracerebral implants can be functionally integrated with the host brain, particularly in man, is still poorly understood and remains a topic for further clinical investigation. The chances for extensive integration may be greatest for very small neural grafts or cell suspensions. Re-innervation of these small, solid grafts seems to be a function of the rapid availability of a rich vascular bed or contact with cerebral spinal fluid. Evidence suggests that the grafts may be revascularized very quickly, perhaps within hours, especially as cell suspensions (Leigh et al., 1994). The results of these types of cell replacement therapies are encouraging, but heterogeneity of transplanted cells, risks for immunological rejection and other problems related to the transplantable material have raised numerous concerns about cell-based therapies.

Fetal Dopaminergic Neurons

Clinical data clearly demonstrate that fetal mesencephalic dopamine neurons obtained from a human fetus can survive and function in the brains of patients with Parkinson's disease. Unfortunately, functional recovery after transplantation has been only partial, and both the reproducibility and efficacy of the procedure must be significantly improved. Nevertheless, early publications on transplantation of fetal dopaminergic neurons have demonstrated success. In a study from Great Britain an initial 12 patients had fetal tissue from a single donor placed stereotactically into the caudate (Hitchcock et al., 1989). The patients showed improvement within one week and levodopa dosage (the more traditional therapy) was reduced by 29% within the first three months and by 24% within the first six months. Follow-up on nine patients demonstrated a 29% improvement in the Webster rating scale at three months and a 42% improvement at six months. Other early reports indicated similar improvement (Freed et al., 1989). Since the late 1980's, when human fetal tissue transplants began, it has been estimated that over 500 patients with Parkinson's disease have received fetal implants. The results in two series of experiments in the United States have been reported. Freed et al. have made observations in seven patients followed from 12 to 46 months after mesencephalic fetal transplants (Freed et al., 1992). Two of these patients had unilateral implants into the caudate and putamen and five had bilateral implants into the putamen only. Long-term moderate improvement was reported, and the Sinemet dosage was substantially reduced. The improvement was related to the presence or absence of immunosuppressant drugs. In another series of experiments the improvement appeared to be more mild (Spencer et al., 1992). These less impressive results may be related to the cryopreservation of the transplanted fetal tissue and the older age of the tissue. A major conclusion from these results is that implantation of fetal dopamine-rich mesencephalic tissue can lead to a therapeutically valuable, sustained improvement in motor function in patients with idiopathic Parkinson's disease (see Lang and Lozano, 1998).

The main limitations of current fetal cell-transplantation procedures are the practical, ethical and safety issues related to the use of fetal tissue. The large number of fetal dopaminergic neurons that are needed to obtain therapeutic effects in patients restricts the applications of transplantation procedures to highly specialized medical centers. Current transplantation techniques result in survival of 5-20% of the transplanted neurons. Consequently, cells from 3 to 5 fetuses yield only 100,000-150,000 surviving dopaminergic neurons (Lindvall, 1997). Animal experiments have demonstrated that inhibition of cell death by caspase inhibitors, free radical scavengers, and neurotrophic factors may increase dopamine neuron survival 2 to 3 fold (Sinclair et al., 1996, Zawada et al., 1998, Schierle et al., 1999). Application of these additions to human clinical protocols may increase the cell survival and reduce the number of fetal cells required for efficient therapeutic effect. The main focus of current research is developing techniques to improve survival and growth of transplanted dopaminergic neurons.

Autologous Adrenal Medulla Grafts

Backlund and his group in Stockholm, Sweden started human transplants based on experimentation by collaborators in Lund, Sweden. In their experiments, cell suspensions were stereotactically placed into the caudate. Although their results were not spectacular, probably because they implanted relatively pure suspensions of neurons without associated glial cells, their experiments opened up the field to other investigators. Subsequently, Dr. Ignacio Madrazo and Dr. Drucker-Colin described a series of 54 patients with Parkinson's disease who showed marked improvement in their disease some months after they had received a transplant of autologous adrenal medulla to the caudate nucleus of their brain (Madrazo et al., 1987). Their success seems stem from changing their protocol so that they implant very small pieces of adrenal gland (and, more recently, fetal grafts that have open access to cerebral spinal fluid so that graft viability is maintained until neovascularization). Following Madrazo's results, Allen et al., at Vanderbilt University and Jiao et al. in Beijing, China, reported on multiple patients with severe Parkinson's disease who had improved after undergoing a technique very similar to Madrazo's.

CNS Stem Cell Propagation, Differentiation and Transplantation

An alternative approach to treating a neurodegenerative disease such as Parkinson's disease is to take tissue from a patient or donor, isolate the central nervous stem cells from the tissue, cause the stem cells to differentiate into the desired type of neurons, and implant the neurons into the appropriate region in the patient's brain. This approach is referred to as autologous transplantation because the cells are taken from a patient and implanted into the same patient. The same process could be applicable to many neuronal diseases and disorders in addition to Parkinson's disease. For example, the process could be used to treat spinal cord damage.

Following removal of an appropriate tissue sample, the process would involve three steps: isolation, propagation, and differentiation. In the isolation step, stem cells are preferably separated from all the other cells in a tissue sample. Alternatively, the tissue may be placed in a chemical environment that preferentially facilitates the growth of stem cells. In the propagation step the stem cells are kept alive and preferably encouraged to multiply, for example from a few cells into tens of thousands of cells. In the differentiation step, the cells are preferably caused to develop into the type of cell that is suitable for the application. For example, in the case of a Parkinson's patient, at least a portion of the stem cells are preferably caused to develop into neurons. Following differentiation, the differentiated cells may be implanted into the patient. In the case of a Parkinson's patient, the differentiated cells would preferably be implanted in the patient's brain. For the treatment of spinal cord injury, the differentiated cells would be placed in the spinal cord at or near the site of injury.

Although such treatments have been contemplated, there continues to be a need for actual compositions and methods for isolation, propagation, and differentiation of stem cells for treating nervous system pathologies.

SUMMARY OF THE INVENTION

In one aspect, the invention provides compositions and methods for the isolation, propagation, and differentiation of cells for treating pathologies. The cells that are propagated include stem cells. In another aspect, the invention provides treatments for neurotrauma and neurodegenerative diseases, including Parkinson's disease. These compositions, methods and treatments may be used in a wide variety of autologous and homologous cell therapy applications, including, without limitation, replacement of lost and defective cells and delivery of therapeutic products. Other applications include drug design and drug testing.

According to certain embodiments, the present invention provides methods for treating neurodegenerative disorders, including by not limited to, Alzheimer's disease, Parkinson's disease, Huntington's chorea, amyotrophic lateral sclerosis and other motor neuropathies. According to certain other embodiments the present invention provides methods for treating patients with nervous system damage, including, but not limited to, central nervous system ("CNS") trauma (e.g., spinal cord injury) and strokes.

In one embodiment, a method is provided for treating a patient suffering from a central nervous system disorder. Central nervous system stem cells are obtained and differentiated by culturing in vitro in differentiation medium. The differentiation medium preferably comprises FGF8 and GDNF. Following differentiation the cells are transplanted into the central nervous system of the patient.

The central nervous system neurons may be obtained from the patient or from an unrelated donor. In one embodiment the CNS stem cells are obtained by surgically removing a sample of central nervous system tissue from the patient, preferably a sample of cortex from the patient's frontal lobe.

In one embodiment the differentiation medium additionally comprises one or more compounds selected from the group consisting of all-trans retinoic acid (RA) and dibutyryl cyclic AMP (dBcAMP). In a particular embodiment the differentiation medium comprises $10^{-6}$ RA, 1 mM dBcAMP, 20 ng/ml FGF8 and 20 ng/ml GDNF.

In another embodiment, the CNS stem cells are proliferated in vitro prior to differentiation. The CNS stem cells are preferably proliferated by culturing them in proliferation medium comprising bFGF, LIF and EGF. In a particular embodiment the proliferation medium comprises 20 ng/ml bFGF, 20 ng/ml LIF and 20 ng/ml EGF.

In one embodiment the stem cells are differentiated for three days prior to transplantation.

In another embodiment the patient is suffering from Parkinson's disease. In this case, the differentiated cells are preferably transplanted into the caudate nucleus in the patient's brain. In a further embodiment the patient is suffering from an acute spinal cord injury.

In a further aspect, the invention provides a method of treating a patient suffering from Parkinson's disease by obtaining CNS stem cells from the patient, proliferating the stem cells by culturing the cells in a first medium comprising bFGF, LIF and EGF, differentiating the cells by culturing the cells in a second medium comprising RA, dBcAMP, GDNF and FGF8, and transplanting the differentiated cells into the patient's brain. In one embodiment the cells are differentiated for about three days prior to transplantation. Preferably the cells are transplanted into the caudate nucleus and/or putamen in the patient's brain. The patient preferably receives from about 0.5 million to about 80 million cells, more preferably about 0.5 million to about 10 million cells, and still more preferably 4 million to about 8 million cells.

The CNS stem cells are preferably obtained from the cortex of the patient during craniotomy.

In one embodiment the first medium comprises about 0.2 to about 200 ng/ml each of bFGF, LIF and EGF, more preferably about 20 ng/ml of each.

In another embodiment the second medium preferably comprises about $10^{-8}$ to about $10^{-4}$ M RA, about 0.01 to about 3 mM dBcAMP, about 0.02 to about 200 ng/ml FGF8, and about 0.02 to about 200 ng/ml GDNF, more preferably about $10^{-6}$ M RA, about 1 mM dBcAMP, about 20 ng/ml FGF8 and about 20 ng/ml GDNF.

A cell culture medium for stimulating the proliferation of CNS stem cells is provided that comprises basic fibroblast growth factor (bFGF), leukemia inhibitor factor (LIF), and epidermal growth factor (EGF), preferably in an amount that is sufficient to support proliferation of stem cells. The stem cells are preferably central nervous system stem cells, more preferably human central nervous system stem cells. In one embodiment the preferred concentration of bFGF, LIF, and EGF is each from about 0.2 to about 200 ng per ml of the medium. More preferably the concentration of bFGF, LIF and EGF is each within the range of about 2 to about 200 ng/ml, and yet more preferably about 5 to about 50 ng per ml. Even more preferably the medium comprises about 20 ng/ml each of bFGF, LIF and EGF. In one embodiment the medium additionally comprises B27 (GIBCO) supplement.

A method of stimulating the proliferation of stem cells, preferably CNS stem cells, is also provided, comprising culturing the stem cells in cell culture medium comprising bFGF, LIF and EGF.

A cell culture medium for differentiating stem cells, preferably CNS stem cells, is also provided. The medium preferably comprises an amount of Fibroblast Growth Factor Eight (FGF-8) and Glial Cell Line-Derived Neurotrophic Factor (GDNF) that supports the differentiation of at least a portion of a treated population of stem cells into a neuronal phenotype. In one embodiment the medium preferably comprises about 0.02 to about 200 ng FGF-8 and about 0.02 to about 200 ng GDNF per ml of medium in which the stem cells are cultured. In a further embodiment, the composition additionally comprises all-trans retinoic acid (RA) and/or dibutyryl cyclic AMP (dBcAMP). In a particular embodiment RA is preferably present in the medium at a concentration of about $10^{-8}$ to about $10^{-4}$ M. In another embodiment dBcAMP is preferably present in the medium at a concentration of about 0.01 to about 3 mM. More preferably the culture medium comprises about $10^{-6}$ RA, about 1 mM dBcAMP, about 20 ng/ml FGF8 and about 20 ng/ml GDNF.

A method is also provided for stimulating the differentiation of stem cells, preferably CNS stem cells, comprising culturing the stem cells in vitro in culture medium comprising RA, dBcAMP, FGF8 and GDNF.

In one aspect, the invention includes methods of treating brain cells, including stem cells, taken from a patient suffering from a neurodegenerative disease. In one embodiment the patient is human. The methods are preferably performed on stem cells that have been removed from a patient and are being cultured in vitro in a medium, but prior to the reimplantation of the cells into the patient's central nervous system. In one embodiment, stem cells that have been removed from a patient are cultured in a composition that stimulates stem cell propagation. The composition preferably comprises basic fibroblast growth factor (bFGF), leukemia inhibitor factor (LIF), and epidermal growth factor (EGF). In one embodiment the preferable concentration of bFGF, LIF, and EGF is about 0.2 to about 200 ng each per ml of cell culture medium, more preferably about 2 to about 200 ng per ml and even more preferably about 5 to about 50 ng per ml.

In another embodiment the stem cells are cultured in a composition that stimulates stem cell differentiation. The composition preferably comprises an amount of Fibroblast Growth Factor Eight (FGF-8) and Glial Cell Line-Derived Neurotrophic Factor (GDNF) that supports the differentiation of at least a portion of a treated population of stem cells into a neuronal phenotype. In one embodiment the composition preferably comprises about 0.02 to about 2000 ng FGF-8 and about 0.02 to about 2000 ng GDNF per ml of medium in which the stem cells are cultured. In a further embodiment, the composition preferably additionally comprises all-trans retinoic acid (RA) and/or dibutyryl cyclic AMP (dBcAMP). In a particular embodiment RA is preferably present in the medium at a concentration of about $10^{-8}$ to $10^{-4}$ M. In another embodiment dBcAMP is preferably present in the medium at a concentration of about 0.01 to about 3 mM.

In yet another aspect, the invention includes methods for treating a patient suffering from a neurodegenerative disease by culturing stem cells taken from the patient in one or more compositions that support the proliferation and/or differentiation of the stem cells. The cells are then transplanted back into the patient in a location chosen to maximize the therapeutic benefit. In one aspect a patient suffering from Parkinson's disease is treated. Stem cells are obtained, preferably central nervous system stem cells, and at least a portion of the cells are caused to differentiate into dopaminergic neurons. The differentiated cells are implanted into the brain of a patient. In another embodiment, a patient suffering from spinal cord trauma is treated. In this embodiment, stem cells are obtained and at least a portion of the stem cells are caused to differentiate into GABAergic cells. The differentiated cells are implanted into the spinal cord of the patient. In another embodiment, neurons are implanted into the central nervous system of a patient at or near a pattern-generation portion of the central nervous system. Preferably, stem cells are obtained from the patient to be treated. Alternatively, they may be obtained from a related or unrelated donor. Compositions described above may be used to cause the stem cell to propagate and differentiate into GABAergic and/or dopaminergic neurons.

In a further aspect, the invention includes methods for causing stem cells to differentiate into one or more of a variety of neuronal cell types, including cholinergic, dopaminergic, and glutamatergic neurons.

Differentiation of the stem cells in vivo is not required in the methods of the present invention. However, in some embodiments further differentiation may occur in vivo. The methods of the invention allow control of the numbers and types of cells while the cells are in vitro. In some embodiments the methods of the invention are used with stem cells taken from a patient into whom the cells will be transplanted back following in vitro propagation and/or differentiation (autograft). In other embodiments the stem cells for use in the methods are obtained from a person other than the patient to be treated, as in a homologous graft. Or the techniques could be used for treating cells derived from an animal source and the resulting cells could be transplanted into humans (xenograft).

The invention is described in terms of certain embodiments set forth herein; these embodiments are not meant to limit the scope or spirit of the invention. Other variations of the embodiments described herein will be apparent to those skilled in these arts.

DETAILED DESCRIPTION OF THE PREFERRED EMBODIMENT

The treatment of human neurodegenerative diseases and neurotrauma by cell replacement or transplantation requires a reliable source of neuronal cells. CNS stem cells are preferable because of the ability to propagate and differentiate the cells in vitro. IN addition, the use of CNS stem cells overcomes many of the technical and ethical problems associated with the use of fetal tissue.

Methods for isolating CNS stem cells, propagating and differentiating them in culture and using them to treat neuronal disorders are described herein.

It has been demonstrated that the entire ventricular neuroaxis including spinal cord of the adult mammalian central nervous system (CNS) contains multipotent stem cells ("CNS stem cells" or "neuronal stem cells"; Morshead and van der Kooy, 1992, Reynolds and Weiss, 1992, Lois and Alvarez-Buylla, 1993, 1994, Morshead et al., 1994, Weiss et al., 1996a, b). The isolation of putative stem cells form the embryonic (Davis and Temple, 1994) and adult rodent CNS (Reynolds and Weiss, 1992, Lois and Alvarez Buylla, 1993, Gritti, et al., 1996, Suhonen et al., 1996) has been accomplished by means of growth factor stimulation.

Multipotent stem cells are localized in the proliferative zones of the developing and adult nervous system. However, in rodents, CNS stem cells reside in a variety of locations in the nervous system (Palmer et al., 1999) including areas where there is no detectable neurogenesis, such as in the optic nerve and spinal cord. Fetal stem cells have been isolated form several areas including spinal cord (Vescovi et al., 1999, Carpenter, et al., 1999), while adult stem cells have been isolated from hippocampus, subventricular zone, cortex and neocortex (Kukekov et al., 1999; unpublished data). Neuronal stem cells are localized, for example, in the ependymal zone of the brain and spinal cord. Continuous neurogenesis also occurs in the dentate gyrus of the hippocampus (Altman and Das, 1965, Bayer et al., 1982, Cameron et al., 1993). Palmer et al (1995) demonstrated that basic fibroblast growth factor supports proliferation of hippocampus neuronal stem cells in vitro.

Regional and temporal differences in the expression of regulatory genes in the proliferative compartment suggest the presence of different stem cell populations. Differences in fetal and adult CNS stem cell populations have been identified by characterizing the developmental potential of neurospheres derived from naturally aborted fetal and adult human brain. Analysis of the expression patterns of regulatory genes known to be important for neuronal differentiation (maturing) shows that fetal and adult human CNS stem cell isolates display similar proliferation kinetics, differentiate into the three major cell types of the nervous system, and express similar sets of regulatory genes (Palm et al., 2000). However, each of the individual CNS stem cell isolates could be distinguished by its specific gene expression and developmental potential.

Nervous system stem cells have been isolated from human embryonic and adult brain (Svendsen et al., 1997, Chalmers-Redman et al., 1997, Vescovi et al., 1999, Kukekov et al., 1999). These cells survive transplantation into the adult rodent brain, and differentiate into neurons and glia with no subsequent tumor formation (Svendsen et al., 1997, Vescovi et al., 1998, Fricker, et al., 1999). Further, neuronal stem cells have an extended self-renewal capacity and possess the potential to give rise to all three major brain cell types. Human CNS stem cell lines display remarkable functional stability, as their growth characteristics, dependence of growth factors, and potential for neuronal differentiation remain unchanged over extensive subculturing (Vescovi et al., 1999, Fricker et al., 1999, Carpenter et al., 1999, our unpublished data). In addition, the expression of late neuronal antigens such as neurofilament proteins and the acquisition of distinct neuronal electrophysiological properties show that even the progeny of long-term cultured stem cells can accomplish full neuronal maturation. As a result, virtually unlimited numbers of neuronal cells could be generated under standardized conditions. Several laboratories have cultured human stem cells in vitro without detectable changes in growth characteristics and differentiation potential for prolonged periods, up to several years (Capenter et al., 1999; Vescovi et al., 1999; unpublished data).

Stem cells also provide the unprecedented opportunity to control some critical parameters in clinical transplantation. Neuronal stem cells differentiate spontaneously into neurons, astrocytes, and oligodendrocytes after plating onto substrates which stimulate adhesion and differentiation, for example poly-L-omithine or laminin. In addition, these multipotent CNS stem cells proliferate and expand in response to epidermal growth factor ("EGF") and basic fibroblast growth factor ("bFGF") and differentiate into neurons, astrocytes and oligodendrocytes (Reynolds and Weiss, 1992, Morshead et al., 1994, Weiss et al., 1996b). Human CNS stem cells continue to proliferate in vitro in the presence of bFGF and EGF (Svendsen et al., 1997; Kukekov et al. 1999) or LIF (Carpenter et al. 1999; Fricker et al., 1999).

In view of the advantages described above, multipotent CNS stem cells and their derivatives represent an ideal cell population for cell based therapies. However, in order for stem cells to form useful connections with host neurons following transplantation, the stem cells must differentiate into a useful neuronal type for the particular situation. Thus the phenotype (neurotransmitter profile, neurotransmitter and other membrane receptors, second messenger systems) of new neurons generated from the differentiation of stem cells preferably corresponds to the phenotype of neurons at the site of injury. Cell morphology and expression of neuronal cell type specific antigens may be analyzed to evaluate neuronal differentiation. For example, antibodies to nestin may be used as markers of stem cell phenotypes. Expression of neurofilament L and M, neuronal specific enolase, and GAP-43 may be used as general neuronal markers.

Progress in transplantation experiments suggests that CNS stem cells can be successfully used as a neuronal replacement after CNS injury. In the ideal situation the transplanted stem cells will differentiate into the types of neurons which will make correct connections (synapses) and serve as a substrate for descending and ascending long fiber tract neurons. Unfortunately, stem cells differentiate mostly into astrocytes after transplantation. Additionally, after transplantation, neuronal stem cells differentiate into neurons in the areas of the nervous system where neurogenesis occurs in the adults, such as dentate gyrus of the hippocampus and olfactory bulb, but not in other regions. These data indicate that signals that are necessary for neuronal differentiation are missing in most parts of the adult nervous system, including the spinal cord. Thus, in order to successfully use neuronal stem cells in transplantation therapeutically it will be important to initiate neuronal differentiation of stem cells before transplantation. Methods are provided herein for propagating stem cells in vitro, causing stem cells to differentiate into particular types of neurons and methods for treating patients suffering from CNS injury or disease or disorder by transplantation of differentiated stem cells.

The present invention is based, in part, on the experimental finding that adult human brain contains neuronal stem cells that can be isolated, propagated in vitro and differentiated into dopamine secreting neurons. The dopamine producing neurons survive transplantation into animal and human striatum and are therapeutically beneficial in the treatment of Parkinson's disease. By manipulating the environment during differentiation, stem cells can be caused to differentiate into other neuronal types, such as GABAergic neurons.

In one aspect the invention provides methods of treating cell samples that include stem cells, preferably taken from patient suffering from a neurodegenerative disease. The methods are preferably performed while the cells are cultured in vitro in a medium and prior to the reimplantation of the cells into the patient's central nervous system for therapy of the neurodegenerative disease. The methods may include the step of culturing the stem cells in a composition comprising an amount of basic fibroblast growth factor (bFGF), leukemia inhibitor factor (LIF), and epidermal growth factor (EGF) that is sufficient to support proliferation of the stem cells in vitro. In addition, prior to transplantation the stem cells are preferably cultured in a medium comprising an amount of Fibroblast Growth Factor Eight (FGF-8) and Glia Derived Neurotrophic Factor (GDNF) that is sufficient to support differentiation of at least a portion of a group of the stem cells into a neuronal phenotype. The medium preferably further includes RA and dBcAMP. In a preferred embodiment the methods are used to produce dopaminergic cells that are implanted into the brain of a patient suffering from Parkinson's disease. In another embodiment the methods are used to make GABAergic neurons that are implanted into the brain or spinal cord of a patient. The preferred implantation site is the pattern generator.

In one embodiment of the present invention, human CNS cells that include neuronal stem cells are differentiated in vitro, resulting in the production of dopaminergic neuronal cells that can be used to replace lost dopaminergic neurons in the brain of a patient suffering from Parkinson's disease. Stem cells are preferably isolated from the patient's own brain (autologous transplantation). Alternatively, stem cells may be isolated from a related donor, an unrelated donor of the same species, or a donor from a different species. Stem cells are preferably initially propagated in vitro in the presence of growth factors. Prior to transplantation, cells are transformed into dopamine producing cells, as well as other cells.

A purified culture of treated cells may be prepared for administration to a patient suffering from Parkinson's disease. The preparations preferably contain approximately 0.5 to 80 million cells and more preferably contain 0.5 to 20 million cells, and still more preferably 4-10 million cells. A preparation preferably contains dopamine secreting neurons representing about 5 to about 30% of the neuronal cells in the preparation. Methods are included for screening the cells for differentiation (cell type and activity), presence of adventitious agents, purity, sterility, mycoplasma, and endotoxins. Testing for differentiation is preferably performed about four months after initiation of stem cell culture.

A. DEFINITIONS

The terms "CNS stem cell" and "neuronal stem cell" refer to multipotent cells obtained from the central nervous system that can be caused to differentiate into cells that posses one or more biological activities of a neuronal cell type.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development of a disorder or altering the pathology of a disorder. Accordingly, "treatment" refers to both therapeutic treatment and prophylactic or preventative measures. Specifically, the treatment may directly prevent, slow down or otherwise decrease the pathology of cellular degeneration or damage, such as the pathology of nerve cells, or may render the cells, e.g. neurons, more susceptible to treatment by therapeutic agents. In a preferred embodiment, the treatment reduces or slows down the decline and/or restores function.

The term "patient" refers to those in need of treatment, including those already with a disorder as well as those in which a disorder is to be prevented.

The "pathology" of a (chronic) neurodegenerative disease or acute nervous system injury includes all phenomena that affect the well being of the patient including, without limitation, neuronal dysfunction, degeneration, injury and/or death.

The terms "CNS disease" and "CNS disorder" are used in the broadest sense and include any condition that is associated with the central nervous system and would benefit from treatment of the present invention. This includes chronic and acute disorders or diseases including those pathological conditions which predispose the mammal to the disorder in question. A preferred disorder to be treated in accordance with the present invention is Parkinson's disease. The terms include, without limitation, neurodegenerative disorders as well as trauma or acute injury.

The terms "neurodegenerative disease" and "neurodegenerative disorder" are used in the broadest sense to include all disorders the pathology of which involves neuronal degeneration and/or dysfunction, including various conditions involving spinal muscular atrophy or paralysis; and other human neurodegenerative diseases. Neurodegenerative diseases include, without limitation, Alzheimer's disease and Parkinson's disease. In a preferred embodiment, the neurodegenerative disease that is treated by the methods disclosed herein is Parkinson's disease.

"Mammal" for purpose of treatment refers to any animal classified as a mammal, including humans, domestic and farm animals, and zoo, sport or pet animals, such as dogs, horses, sheep, cats, cows, etc. Preferably, the mammal is human.

"Dopaminergic neuron," is used broadly herein and refers to any cell that contains the neurotransmitter dopamine. Similarly, "GABAergic neuron" as used herein, refers to any cells that contain the neurotransmitter GABA. Expression of enzymes involved in the synthesis or degradation of the different neurotransmitters is preferably analyzed to determine specificity of neuronal differentiation. For example, dopaminergic neurons may be identified by positive staining for tyrosine hydroxylase (TH) or dopa decarboxylase (DDC).

Propagation of Cells In Vitro

Stem cells for use in the methods disclosed herein are not limited in any way and may be obtained from any source. Preferably the stem cells are neuronal stem cells that are obtained from a mammalian source. For example, they may be obtained from the central nervous system of an adult, juvenile or fetal mammal, preferably a human. Alternatively, the stem cells may be obtained from an available in vitro culture of neuronal stem cells. Regardless of the technique used, both stem cells and fully differentiated cells are obtained.

In one embodiment a tissue sample is obtained from the central nervous system of a mammal. The sample may be obtained by any method known in the art, such as by biopsy or by a surgical procedure. Such methods for obtaining tissue samples are well known in the art. The sample is preferably obtained from a part of the central nervous system that is known to comprise stem cells.

In a preferred embodiment, a small tissue sample is obtained from a donor during a craniotomy procedure. The sample may be, for example, a sample of cortex. Preferably, the donor is the patient that will receive an autologous transplant of differentiated cells.

In a particular embodiment, a stereotactic biopsy of the temporal periventricular ependyma following sterotactic MRI of the brain is performed under local anesthesia. The selected temporal region is preferably of the non-dominant hemisphere. The periventricular ependyma is preferably reached from an orthogonal approach to the anterior temporal lobe.

Optionally, the tissue sample is cut into small pieces, preferably from about 0.1 to about 10 mm$^3$, more preferably from about 0.5 to about 1 mm$^3$.

The tissue sample is treated to dissociate individual cells by any method known in the art. In one embodiment the tissue sample is transferred into trypsin solution that preferably comprises about 0.02 mg trypsin/ml in Verseen (Gibco). The tissue is incubated at 37° C. for approximately 10-20 minutes, after which trypsin inhibitor is added.

The sample is triturated mechanically, such as with a Pasteur pipette and the cell suspension is centrifuged, the pellet washed with culture media and the cells are plated.

Preferably the cells are plated at a density of about 5,000 to about 10,000 viable cells/ml culture media in tissue culture dishes, such as 6 well Nunc dishes.

The cells are cultured in culture media that comprises growth factors that stimulate proliferation. The culture media comprises one or more growth factors selected from the group consisting of basic fibroblast growth factor (bFGF), leukemia inhibitor factor (LIF), and epidermal growth factor (EGF). Preferably the culture medium comprises amounts of bFGF, LIF and EGF that are sufficient to support proliferation of the stem cells. More preferably the culture media comprises bFGF, LIF, and EGF at a concentration of about 0.2 to about 200 ng each per ml of the medium, even more preferably at a concentration of from about 2 to about 200 ng each per ml of the medium; and yet more preferably at a concentration of from about 5 to about 50 ng each per ml of the medium.

In one embodiment the medium comprises DMEM/F-12, 20 ng/ml bFGF and 20 ng/ml LIF. In another embodiment the medium additionally comprises 20 ng/ml EGF. In a further embodiment the medium comprises B27 supplement (Gibco).

The cells are preferably grown as neurospheres. They may be propagated in vitro in the culture medium for any length of time. Preferably the media is changed about every third day, and neurospheres are dissociated by mechanical trituration every 10 to 15 days.

Optionally the cells may be passaged at high density (about $10^4$ to about $5 \times 10^4$ cells/mm$^2$) every 10 to 15 days.

When desired, the cells may be used in transplantation therapy. Preferably, however, the cells are first differentiated, as described below.

Differentiation of CNS Stem Cells into Neurons In Vitro

One of the greatest advantages of using stem cells for transplantation is that cell differentiation can be initiated when desired and fine-tuned by modifying the growth conditions. A very small portion of human stem cells naturally differentiate into dopaminergic neurons (tyrosine hydroxylase (TH)—positive) upon withdrawal of growth factors and initiation of differentiation. Svendson (1997) reported that less than 0.01% of total cells become TH positive in vitro. Treatment of stem cells with a combination of IL-1b, IL-11, and GDNF induces formation of more neurons in cell culture (Carpenter et al., 1999).

Development and survival of substantia nigra dopaminergic neurons depends on the expression of orphan nuclear hormone receptor Nurr1 in these cells and over-expression of Nurr1 in stem cells stimulates dopaminergic differentiation when these cells are exposed to glial condition media (Wagner et al., 1999). Also other laboratories have reported effect of glial conditioned media on differentiation of dopaminergic neurons (Daadi and Weiss, 1999). Analysis of development of mesencephalic neurons during embryogenesis has revealed that sonic hedgehog (SHH) and FGF8 are essential for development of mesencephalic dopaminergic neurons (Ye et al., 1998). Unfortunately, treatment of stem cells with SHH and FGF8 does not increase the number of TH positive cells in CNS stem cell cultures. There are reports (Studer et al., 1998) that expansion of precursor cells in the presence of bFGF results in significant differentiation of dopaminergic neurons. Large clusters of differentiated neurons contained 18% dopaminergic neurons.

Treatment of human CNS stem cells growing as neurospheres with all-trans retinoic acid, dibutyryl cAMP, FGF8, and GDNF was found to cause differentiation of neuronal stem cells into dopaminergic neurons. Without treatment, less than 1% of differentiated cells were TH positive while after treatment about 5-30% of differentiated cells were TH positive.

Neuronal stem cells are caused to differentiate by culturing the cells in a differentiation media that comprises one or more factors that stimulates differentiation. Cells are preferably plated on poly-omithine or laminin coated tissue culture plates and contacted with the differentiation media. Cells are preferably dissociated into smaller aggregates of about 50 to about 200 cells prior to plating by mechanical trituration. Approximately 2×106 cells are plated, for example, on 100 mm tissue culture plates.

Preferably the media comprises one or more factors selected from the group consisting of fibroblast growth factor 8 (FGF8), glia derived neurotrophic factor (GDNF); all-trans retinoic acid (RA) and diburyry cyclic AMP (dBcAMP). The cells are preferably cultured in the differentiation media for approximately 1 to 6 days, more preferably for about 3 days, prior to being used for transplantation, as described below.

In one embodiment the neuronal stem cells are cultured in media comprising an amount of Fibroblast Growth Factor 8 (FGF-8) and/or Glia Derived Neurotrophic Factor (GDNF) that is sufficient to support differentiation of at least a portion of a group of the stem cells into a neuronal phenotype. In one embodiment the preferred concentration of FGF-8 and GDNF in the medium is about 0.02 to about 200 ng each per ml of medium.

In another embodiment the neuronal stem cells are incubated in media that comprises all-trans retinoic acid (RA) and dibutyryl cyclic AMP (dBcAMP). The preferred concentration of RA in the medium is about $10^{-8}$ to about $10^{-4}$ M, more preferably about $10^{-6}$ M to about $10^{-4}$ M, and the preferred concentration of dBcAMP in the medium is about 0.01 to about 3 mM, more preferably about 1 mM.

In a further embodiment, the neuronal stem cells are incubated in media that comprises RA, dBcAMP, FGF8 and GDNF. Preferably, the concentration of RA is about 10-6 M, the concentration of dBcAMP is about 1 mM, the concentration of FGF8 is about 20 ng/ml and the concentration of GDNF is about 20 ng/ml.

The media is preferably F12/DMEM serum free medium supplemented with B27 growth supplement (Gibco) as well as the desired differentiation factors as described above.

Following differentiation, cells are preferably collected by mild trypsinization (about 0.01% trypsin in Verseen), washed twice with D-PBS and resuspended in a small volume of D-PBS. In a typical experiment, differentiation for three days yields about 0.7 to about 2 million dopaminergic cells. However, a much wider range of dopaminergic cells can be obtained depending on the volume and source of the original cells.

For the treatment of Parkinson's disease, a culture having 5% to 30% of the neurons as dopaminergic neurons is preferably used for transplantation.

Transplantation of Human CNS Stem Cells

Following proliferation and differentiation, neuronal stem cells are transplanted into a patient. Preferably the patient will receive from about 0.5 million to about 80 million cells, more preferably about 0.5 million to about 10 million cells, and still more preferably 4 million to about 8 million cells. In a preferred embodiment, this corresponds to about 25,000 to about 24,000,000 dopaminergic neurons, more preferably about 25,000 to about 3,000,000 dopaminergic neurons, and still more preferably 200,000 to about 2,400,00 dopaminergic neurons. Prior to transplantation, cells are preferably washed at least 3 times with PBS to reduce the level of growth factors from the differentiation media.

In the preferred embodiment, neuronal stem cells are investigated to determine the proportion of the type of neuron of interest prior to transplantation.

The patients will have the cells implanted following standard surgical procedures. The cells may be implanted anywhere in the central nervous system. The exact location will depend upon the type of neuronal disorder from which the patient is suffering, as well as the patients particular pathology. One of skill in the art can determine the location of the transplant and optimize the transplantation procedure.

In one embodiment a patient suffering from Parkinson's disease is transplanted with cells differentiated as described above. The patient will have the surgery performed under local anesthesia in an operating room. The differentiated cells are implanted in the caudate nucleus and putamen, preferably bilaterally using stereotactic techniques. Preferably the implantation is MRI-guided.

In a preferred embodiment the stereotactic frame is fixed to the patients skull following administration of local anesthesia. The caudate nucleus and putamen are visualized with MRI. Thereafter, ten passes with very thin sterotactic needles are made about 4 mm apart in the caudate and putamen. Four trajectories for needle tracks in the caudate and six tracks in the putamen are calculated to avoid the posterior limb of the internal capsule. The entry points for the caudate and putamen are preferably at two different sites on the surface.

Within each track, a single cell suspension of 50 μl, averaging about 2 million cells, is slowly delivered, preferably over the course of about 10 minutes.

In transplantation experiments, human stem cell progeny showed an engraftment efficiency comparable to that of fetal tissue in rat brain (Vescovi et al., 1999, Fricker et al., 1999, our unpublished data). Transplantation of untreated CNS stem cells into 6-OH lesioned rat striatum revealed that a small number of dopaminergic neurons develops (Svendsen et al., 1997). They transplanted stem cells, giving less than 0.01% TH positive neurons in vitro, into lesioned brain and observed significant physiological effect in 2 animals using rotation test. The brains of these two animals contained TH positive neurons in the striatum. These experiments suggest that human stem cells have the potential to differentiate into dopaminergic neurons inside the striatum. We also could argue that transplantation of undifferentiated stem cells into Parkinson's disease patients would result in development of dopaminergic neurons and reduction of symptoms. However, transplantation of committed or differentiated dopaminergic neurons will likely have significantly better results.

Articles of Manufacture

In another aspect the invention contemplates an article of manufacture containing materials useful for the collection, propagation, differentiation and transplantation of human CNS stem cells. The article of manufacture comprises one or more containers and a label or package insert on or associated with the container. Suitable containers include, for example, boxes, bottles, vials, syringes etc. The containers may be formed from a variety of materials such as glass and plastic. The containers may hold one or more compounds selected from the group consisting of bFGF, LIF, EGF, FGF8, GDNF, RA and dBcAMP. The containers may also hold other components necessary for the isolation, propagation, differentiation and transplantation of neuronal stem cells. The label or package insert indicates how to use the one or more compounds to cause the stem cells to proliferate and differentiate in vitro into the desired type of neuronal cell. Optionally, the label may also indicate how to use the components of the article of manufacture to obtain stem cells and/or to transplant differentiated cells into a patient.

The foregoing written specification is considered to be sufficient to enable one skilled in the art to practice the invention. Various modifications of the invention, in addition to those shown and described herein, will become apparent to those skilled in the art from the foregoing description and fall within the scope of the appended claims.

It is understood that the application of the teachings of the present invention to a specific problem or situation will be within the capabilities of one having ordinary skill in the art in light of the teachings contained herein.

Further details of the invention are illustrated by the following non-limiting Examples. The disclosures of all citations in the specification are expressly incorporated herein by reference.

Example 1

Isolation and Propagation of Adult Multipotent CNS Stem Cells

Neuronal stem cells were isolated from the brains of 14 adult human patients. Two isolates were obtained from prefrontal cortex, twelve isolates from hippocampus and two isolates from the subventricular zone. A detailed analysis of isolated cells was undertaken for three isolates and compared to fetal stem cells that were isolated from 21 week fetal brain.

CNS stem cells were isolated from the adult hippocampus of three patients with intractable epilepsy and from the 21 week old fetal brain, as described below. Specimens were obtained in accordance with RB protocols obtained through the Cedars Sinai Medical Center, Los Angeles, Calif. (IRB protocol #2475 and 2565).

Isolated stem cells from the adult CNS were cultured as described below and proliferated in vitro as neurospheres expressing nestin and musashi—1 mRNAs, markers that are characteristic of neural stem cells (Lendahl et al., 1990, Sakakibara et al. 1996). Growth characteristics of hippocampal and cortical adult CNS stem cells were similar, with a doubling time of approximately 4 days for both types of neurons. Cells were grown in the presence of basic FGF, EGF and LIF (see below), which are growth factors for neuronal stem cells. On average, variability in growth rates was less than 15%.

To examine developmental potential of adult CNS stem cells, the expression of the cell-type specific markers β III-tubulin, glial fibrillary acidic protein (GFAP), and galactocerebroside (GalC) were analyzed upon differentiation of fetal and adult neurospheres, as described below. The differentiated cells comprised 20-50% astrocytes (GFAP+), 5-30% neurons (β-III-tubulin+) and 1-5% oligodendrocytes (GalC+). Significant variances in the developmental potential of stem cell clones from fetal and adult CNS were not detected. However, the ratio of neurons to astrocytes and oligodendrocytes varied notably from one stem cell isolate to another (Table 1).

TABLE 1

Quantitation of differentiation of individual fetal (F1, F2) and adult (AD1, AD2, AD3) CNS stem cell isolates into neurons, astrocytes and oligodendrocytes. The percentage of neurons, astrocytes and oligodendrocytes was evaluated. Data presented as mean % ± SEM.

| | Stem Cell Isolates | | | | |
|---|---|---|---|---|---|
| | F1 | F2 | AD1 | AD2 | AD3 |
| Neurons (βIII-tubulin) | 5 ± 2 | 23 ± 5 | 11 ± 2 | 30 ± 6 | 19 ± 5 |
| Astrocytes (GFAP) | 50 ± 9 | 29 ± 5 | 46 ± 7 | 49 ± 8 | 20 ± 7 |
| Oligodendrocytes (GalC) | 5 ± 2 | 1 ± 1 | 1 ± 1 | 3 ± 2 | 1 ± 1 |

Isolation of CNS Stem Cells

Resected human brain tissue was placed into ice-cold DMEM/F-12 (GIBCO) containing penicillin-streptomycin, for further dissection. The tissue was cut into small pieces and trypsinized (0.02 mg/ml trypsin in Verseen (GIBCO)) at 37° C. for 5 minutes. After adding trypsin inhibitor mixture (Clonetics), the tissue was mechanically triturated. Cell suspension was centrifuged at 400 rpm for 5 minutes, the pellet was washed once with DMEM/F-12. Cells were plated at density of 5000-10,000 viable cells/ml in media composed of DMEM/F-12, B27 supplement (GIBCO) and growth factors bGFG (20 ng/ml; Peprotec), EGF (20 ng/ml; Peprotec), LIF (20 ng/ml, Peprotec) and penicillin/streptomycin (GIBCO). Stem cells were grown as neurospheres and the media was changed every three days. The neurospheres were dissociated by mechanical trituration every 12-15 days. All further analyses were performed on stem cell isolates with comparable passage number. In cultures which were subsequently used for transplantation into the striatum of Parkinson's patients, antibiotics were omitted 30 days before transplantation.

Counting Cells

Every five days neurospheres were dissociated using trypsin and single cells were counted using hemocytometer after trypan blue straining to identify living cells.

Differentiation of Cells and Immunostaining

Differentiation of neurospheres was initiated by plating cells onto laminin coated tissue culture plates in growth media containing all-trans retinoic acid (RA; $10^{-6}$ M) and dibutyryl cyclic AMP (dBcAMP; 1 mM). Cells were fixed with 4% paraformaldehyde in PBS seven days after plating and immunostained. Antibody against type III β-tubulin (1:500, Sigma) was used to detect neurons, anti-GFAP (1:500, DAKO) to detect astrocytes and anti-GalC (1:25, Rosche) to detect oligodendrocytes. The secondary antibodies that were used were goat anti-mouse FITC (1:200, Sigma) and goat anti-rabbit rhodamine (1:200, Boehringer). Immunostained cells were counted in five separate, randomly chosen fields in each culture using 20× objective. Total cell number was counted using DAPI (Molecular Probes) stained nuclei. The numbers were summed and percentages were calculated.

Conclusion

It was found that adult human CNS contains multipotent stem cells that continue to proliferate in vitro in the presence of appropriate growth factors (bFGF, LIF and EGF) and can be caused to differentiate into neurons, astrocytes and oligodendrocytes. The culture conditions described above make it possible to propagate adult human CNS stem cells in vitro for use in cell replacement therapies, as described herein.

Example 2

Dopaminergic Differentiation of Stem Cells in Vitro

A low ratio of dopaminergic neurons in the progeny of CNS stem cells was observed. As a result, the ability to stimulate differentiation of CNS stem cells into dopaminergic neurons by manipulating the growth conditions was investigated. It has been shown that several growth factors and transcriptional regulators are involved in determining dopaminergic phenotype of mesencephalic neurons. A large number of different growth factors and agents that are known to stimulate neuronal differentiation were tested.

Treatment of dissociated neurospheres with $10^{-6}$ M all-trans retinoic acid (RA), 1 mM dibutyryl cyclic AMP (dBcAMP), FGF8 (20 ng/ml), and GDNF (20 ng/ml) results in development of high number dopamine producing cells, as measured by counting tyrosine hydroxylase (TH) and dopa decarboxylase (DDC) positive cells (Table 2). Analyses of dopamine production and secretion using HPLC analysis also clearly indicated that cell cultures that contain the highest number of TH and DDC positive cells also synthesize and secrete dopamine. Dopamine secretion in these experiments was induced by elevated levels of KCl.

Reverse-phase HPLC analysis demonstrated the neuronal synthesis and secretion of dopamine. Dopamine concentration in culture media of differentiated cells 10 days after initiation of differentiation varied from 0 to 100±45 pg/ml in different stem cell isolates. Stimulation of dopamine secretion by exposing dopamine "positive" cultures to 50 mM KCl for 30 minutes lead to an approximately three-fold increase in dopamine levels in the culture media (345±74 pg/ml, n=3). Levels of dopamine synthesis and secretion correlated well with the ratios of TH and DDC positive cells in culture (Table 2). Thus, cultures with higher number of TH and DDC positive cells also contained more dopamine and secreted more dopamine in response to KCl depolarization. Both the immunostaining and dopamine secretion demonstrate the presence of functional dopaminergic neurons in the treated cultures.

After treatment of cells with RA, dBcAMP, FGF8 and GDNF 10-40% of cells have differentiated into neurons as detected by neurofilament L and beta tubulin III staining. Up to 30% of these neurons express TH and DDC and are considered to be dopamine synthesizing cells. A large variation in dopaminergic differentiation between different stem cell isolates suggests that dopaminergic differentiation preferably be tested during the early phases of culturing of stem cells for transplantation.

In addition to dopaminergic neurons, differentiated cultures contained astrocytes, oligodendrocytes and several other types of neurons. Also, in many cases a population of cells was identified that do not express any of the differentiation markers, indicating that these cells are not neurons, astrocytes or oligodendrocytes but likely remain in an undifferentiated resting stage. The development of GABAergic, cholinergic, glycinergic and glutamatergic neurons was also analyzed in differentiated cultures. Table 3 summarizes the results of differentiation of stem cells.

TABLE 3

Development of astrocytes, oligodendrocytes, GABAergic, cholinergic, glycinergic and glutamatergic neurons from adult human CNS stem cells after treatment with $10^{-6}$ M all-trans retinoic acid (RA), 1 mM dibutyryl cyclic AMP (dBcAMP), FGF8 (20 ng/ml), and GDNF (20 mg/ml).

| Clone | % neurons | % GFAP+ | % GalC | | % GABA | % CHAT | % Glycine | % glutamate |
|---|---|---|---|---|---|---|---|---|
| H1 | 35 ± 6 | 60 ± 3 | 2 ± 1 | 60 ± 8 | 1 ± 1 | 0 | 10 ± 3 | |
| H2 | 11 ± 3 | 55 ± 6 | 1 ± 1 | 90 ± 6 | 0 | | 0 | 0 |
| H3 | 25 ± 4 | 70 ± 7 | 5 ± 3 | 56 ± 8 | 2 ± 1 | 7 ± 3 | 2 ± 1 | |
| H4 | 14 ± 3 | 75 ± 5 | 1 ± 1 | 80 ± 7 | 1 ± 1 | | 1 ± 1 | 1 ± 0 |
| H5 | 25 ± 7 | 55 ± 7 | 5 ± 2 | 95 ± 7 | 0 | | 0 | 0 |
| C1 | 97 ± 7 | 60 ± 5 | 1 ± 1 | 50 ± 7 | 3 ± 3 | 5 ± 3 | 5 ± 2 | |

TABLE 2

Dopaminergic differentiation of adult human CNS stem cells after treatment with $10^{-4}$ M all-trans retinoic acid (RA), 1 mM dibutyryl cyclic AMP (dBcAMP), FGF8 (20 ng/ml), and GDNF (20 ng/ml).

| Cells | % Neurons | % TH+ Cells | % DDC+ Cells | Dopamine pg/ml | Dopamine Secretion pg/ml |
|---|---|---|---|---|---|
| H1 | 35 ± 6 | 13 ± 3 | 12 ± 4 | 100 ± 40 | 350 ± 82 |
| H2 | 11 ± 3 | 0.5 ± 0.02 | 0.5 ± 0.01 | 0 | 0 |
| H3 | 24 ± 4 | 27 ± 3 | 22 ± 6 | 120 ± 39 | 370 ± 75 |
| H4 | 14 ± 3 | 20 ± 4 | 18 ± 5 | 75 ± 31 | 210 ± 65 |
| H5 | 25 ± 7 | 1 ± 0.1 | 1 ± 0.1 | 0 | 0 |
| C1 | 39 ± 7 | 29 ± 7 | 32 ± 9 | 110 ± 28 | 340 ± 62 |

Methods:

Human CNS stem cells were grown in F12/DMEM serum free media (GIBCO) supplemented with B27 growth supplement (GIBCO), 20 ng/ml each of human recombinant bFGF, EGF and LIF (all from PeproTech, Inc.). CNS stem cells were grown as neurospheres in 25 cm² or 75 cm² Falcon tissue culture flasks. The culture media was changed every second day and neurospheres were dissociated by mechanical trituration every 12-15 days.

To initiate differentiation, cells were plated onto poly-omithine coated tissue culture dishes in F12/DMEM serum free medium (GIBCO) supplemented with B27 growth supplement (GIBCO), $10^{-6}$ M all-trans retinoic acid, 1 mM dibutyryl cyclic AMP, FGF8 (20 ng/ml), and GDNF (20 ng/ml) and cultured 10 days. Before plating cells were dissociated into smaller aggregates (50-200 cells) by mechanical trituration in growth media. Differentiation was evaluated by immunological staining using antibodies against known cell type markers. Cell cultures were fixed for 20 min at room temperature with 4% paraformaldehyde in PBS, washed 3 times in PBS, pH 7.4, permeabilized using a 10 min incubation with 0.1% TritonX-100, and washed again with PBS. Cultures were then incubated in 3% normal goat serum in PBS with 0.1% Tween 20 for at least 1 h at room temperature. Blocking was followed by incubation with primary antibodies in 1% goat serum+0.1% Tween 20 for at lest 2 hours at room temperature. Antibody against type III β-tubulin (1:100, Chemicon) was used to detect neurons and antibody against tyrosine hydroxylase (TH) and dopa decarboxylase (DDC) to detect dopaminergic cells. Antibodies against gamma amino acid decarboxylase (GAD) were used to identify GABAergic neurons (1:1000, Chemicon), anti L-glutamate to detect glutamatergic neurons (1:50, Signature Immunologics), antiglycine to detect glycinergic neurons (1:100, Signature Immunologics) and anticholine acetyl transferase (CHAT) to detect cholinergic neurons (1:100, Chemicon). The cultures were washed in PBS at least 3 times and incubated with secondary antibodies diluted in 1% goat serum with 0.2% Tween 20 for 1 hour at room temperature in the dark. The secondary antibodies were goat anti-mouse FITC (1:200, Sigma) and goat anti-mouse rhodamine (1:200, Boehringer).

HPLC Analysis 1 ml of growth media from growing cultures or cultures that had been stimulated to induce dopamine secretion (by addition of 55 mM KCl for 30 minutes) was collected. Dopamine was immediately stabilized by adding to the culture media 88 μl of 85% orthophosphoric acid and 4.4 mg of metabisulfite. Samples were sent to an HPLC facility where analyses were performed. Dopamine was extracted from samples using the aluminum extraction method and analyzed with a reverse-phase C18 column in a MD-TM mobile phase (Esa Inc.) Results were validated by co-elution with dopamine standards.

Conclusion

Treatment of adult human CNS stem cells propagated in the presence of bFGF, EGF and LIF with all-trans RA, dibutyryl cAMP, FGF8 and GDNF results in differentiation of neurons that synthesize and secrete dopamine. The ratio of differentiated dopaminergic neurons varies in different stem cell isolates from 0 to 30% of the total number of neurons. Additionally, astrocytes, oligodendrocytes and several other types of neurons, including GABAergic, cholinergic, glycinergic and glutamatergic neurons, develop in treated cultures.

Example 3

Transplantation of stem Cell Derived Dopaminergic Cells into Striatum

A major problem related to the transplantation of fetal dopaminergic cells, and other cell types, is the low survival rate of transplanted cells. Current transplantation techniques result in survival of 5-20% of the transplanted neurons. Consequently, cells obtained from 3 to 5 fetuses yield 100,000-150,000 surviving dopaminergic neurons (Lindvall 1997). Using stem cell derived dopaminergic neurons, it is possible to increase the number of transplanted cells as well as to optimize the timing of transplantation.

Transplantation of untreated human CNS stem cells into rat striatum resulted in development and survival of only human astrocytes while transplantation into neurogenic regions such as hippocampus and subventricular zone resulted in development of different neuronal types (unpublished results; Fricker et al., 1999, Vescovi et al., 1999). These results clearly indicate that transplantation of untreated human CNS stem cells into rat striatum results in development of astrocytes and not neurons.

Human CNS stem cell derived dopaminergic neurons were transplanted into rat striatum and analyzed for both survival of neurons and survival of tyrosine hydroxylase (TH) positive cells in particular. Table 4 summarizes the results relating to survival of TH positive cells in rat striatum at 3 weeks and 2 months after transplantation.

It was observed that fully differentiated cells (10 days) do not survive transplantation. An optimal time for transplantation was found to be 2-4 days after initiation of differentiation. Based on these results, 3 day differentiated cells were used in the transplantation experiments described below.

Human CNS stem cells were treated with $10^{-6}$ M all-trans retinoic acid (RA), 1 mM dibutyryl cyclic AMP (dBcAMP), FGF8 (20 ng/ml), and GDNF (20 ng/ml) for 3 days and transplanted into rat striatum. Three different human CNS stem cell isolates H3, H4 and C1 were used in these experiments. Results are shown in Table 4

TABLE 4

Survival of human CNS stem cell derived neurons and TH positive cells three weeks and 2 months after transplantation into rat striatum.

| Clone | Number of Human Cells Counted | % of Neurons | % of TH+ Human Cells |
|---|---|---|---|
| 3 weeks | | | |
| H3 | 3000 ± 50 | 28 ± 8 | 8 ± 4 |
| H4 | 3000 ± 50 | 20 ± 5 | 3 ± 1 |
| C1 | 3000 ± 100 | 50 ± 10 | 15 ± 6 |
| 2 months | | | |
| H3 | 3000 ± 50 | 30 ± 7 | 15 ± 6 |
| H4 | 3000 ± 50 | 15 ± 3 | 1 ± 1 |
| C1 | 3000 ± 50 | 50 ± 9 | 25 ± 7 |

Human anti-nucleus antibodies were used to identify migration of transplanted human cells in rat striatum. More than 80% of transplanted cells had migrated less than 0.5 mm from the transplant site at both 3 weeks and 2 months after transplantation. However, single human cells were detected as far as 5 mm from the transplantation site.

Proliferation of transplanted human cells in rat brain was studied using bromdeoxyuridine (BrdU) labeling. BrdU was intraperitoneally injected into transplanted rats 18 days and 55 days after transplantation (n=3 animals). Animals were euthanized three days after BrdU injection at 21 days and 2 months after transplantation, respectively. Immunohistochemical analysis of BrdU incorporation in brain sections did not reveal any BrdU positive human cells in the transplanted brains. Based on these data, 3 weeks and 2 months after transplantation human CNS stem cells do not proliferate in rat brain.

Methods:

Human CNS stem cells were grown in F12/DMEM serum free media GIBCO) supplemented with B27 growth supplement (GIBCO), 20 ng/ml of human recombinant bFGF, LIF and EGF (all from PeproTech, Inc.). CNS stem cells were grown as neurospheres in 25 cm² or 75 cm² Falcon tissue culture flasks. The media was changed every second day and neurospheres were dissociated by mechanical trituration every 12-15 days.

For stimulating differentiation, cells were plated onto polyomithine coated tissue culture dishes in F12/DMEM serum free medium (GIBCO) supplemented with B27 growth supplement (GIBCO), $10^{-6}$ M all-trans retinoic acid, 1 mM dibutyryl cyclic AMP, FGF8 (20 ng/ml), and GDNF (20 ng/ml) and cultured 3 days. Before plating cells were dissociated into smaller aggregates (50-200 cells) by mechanical trituration in growth media.

Prior to transplantation, cells were differentiated for 3 days as described above, then collected by mild trypsinization (0.01% trypsin in Verseen, 5 minutes at room temperature), washed twice with F12/DMEM medium, resuspended in Dulbecco-modified phosphate-balanced salt solution (D-PBS, GIBCO), washed twice with D-PBS and resuspended in small volume of D-PBS.

Stereotactic surgery was performed under deep ketamin xylazine anesthesia. The immune system of the rats receiving transplants was suppressed by intramuscular injection of cyclosporin every second day. Rats received 3 μl of cell suspension from a 5 μl Hamilton syringe. The cell suspension contained approximately 100,000 cells and was delivered bilaterally in the striatum according to the following coordinates from bregma: Anterior=+0.6, Lateral=2.8 and Ventral −4.8, −4.2. The tooth bar was set at −2.3, and ventral coordinates were taken from dura. Brains were analyzed after 3 weeks (n=4) and 2 months (n=4). Rats were euthanized in a $CO_2$ chamber. Brains were removed and the striatum was dissected and placed in 4% paraformaldehyde overnight. Coronal and sagittal sections were cut on a cryo microtome at a thickness of 15 µm.

Immunohistochemistry

Sections were incubated with primary antibodies following blocking with 3% BSA and 0.02% Tween 20 for 16 hours at 4° C. All primary antibodies were diluted in PBS containing 3% BSA and 0.02% Tween 20. Antibodies used in this study were anti-human nucleus antibodies (1:50 Chemicon), anti-type iii β-tubulin antibodies (1:100 Chemicon) and anti-tyrosine hydroxylase antibodies (1:100, Sigma). For double staining, sections were incubated simultaneously with two primary and secondary antibodies. The secondary antibodies were goat anti-mouse FITC (1:200, Sigma) and goat anti-rabbit rhodamine (1:200, Boehringer).

Example 5

Transplantation of Stem Cell Derived Neurons into Spinal Cord

As discussed above, a major problem related to the transplants of stem cells or stem cell-derived neural cells is the low survival rate of transplanted cells. In addition, transplantation of untreated human CNS stem cells into spinal cord was found to result in development of astrocytes and not neurons. Thus, transplantation of differentiated CNS stem cells into spinal cord was investigated.

Differentiated human CNS stem cell-derived neurons were transplanted into rat spinal cord and analyzed survival of neurons and other cell types. Table 5 summarizes the results of survival of neurons in rat spinal cord 3 weeks and 2 months after transplantation. Fully differentiated cells (10 days) did not survive transplantation. Survival was found to be highest when cells were transplanted 2-4 days after initiation of differentiation. As a result, 3 day differentiated cells in the transplantation experiments.

Human CNS stem cells were treated with $10^{-6}$M all-trans retinoic acid (RA), 1 mM dibutyryl cyclic AMP (dBcAMP), FGF8 (20 ng/ml), and GDNF (20 ng/ml) for 3 days and transplanted into rat striatum. Three different human CNS stem cell isolates H3, H4, and C1 were used in these experiments. Results are shown in Table 5.

TABLE 5

Survival of human CNS stem cell-derived neurons three weeks and 2 months after transplantation into rat spinal cord.

| Clone | Number of Human Cells Counted | % of Neurons |
|---|---|---|
| 3 weeks | | |
| H3 | 3000 ± 50 | 29 ± 8 |
| H4 | 3000 ± 100 | 22 ± 5 |
| C1 | 3000 ± 100 | 51 ± 10 |
| 2 months | | |
| H3 | 3000 ± 100 | 31 ± 7 |
| H4 | 3000 ± 50 | 15 ± 3 |
| C1 | 3000 ± 50 | 49 ± 9 |

Human anti-nucleus antibodies were used to identify migration of transplanted human cells in rat spinal cord. More than 80% of transplanted cells were found to migrate less than 0.5 mm from the transplant site both 3 weeks and 2 months after transplantation. However, single human cells were detected as far as 5 mm from the transplantation site.

Proliferation of transplanted human cells in rat spinal cord was analyzed using bromdeoxyuridine (BrdU) labeling. BrdU was intraperitoneally injected into transplanted rats 18 days and 55 days after transplantation (n=3 animals). Animals were euthanized three days after BrdU injection, 21 days and 2 months after transplantation, respectively. Immunohistochemical analyses of BrdU incorporation in spinal cord sections did not reveal any BrdU positive human cells indicating that 3 weeks and 2 months after transplantation human CNS stem cells do not proliferate in rat spinal cord.

Further, we analyzed survival of specific cell types after differentiation of human CNS stem cell clone C1 cells into GABAergic, cholinergic, glutamateric and glycinergic neurons.

To analyze survival and maintenance of cholinergic and GABAergic neurons, differentiated neurons were transplanted into rat spinal cord. Animals were sacrificed at 30 days and 3 months. Double labeling immunohistochemical staining was used to identify specific human neuronal types in the rat spinal cord. Labeled cells were counted and efficiency of transplantation calculated. Table 6 summarizes the results for survival of GABAergic and cholinergic neurons in rat spinal cord 3 weeks and 2 months after transplantation.

TABLE 6

Survival of GAGAergic and cholinergic neurons developed from the adult human CNS stem cells after transplantation into rat spinal cord.

| Time | Number of Human Cells Counted | % of Neurons | GABAergic/ Cholinergic |
|---|---|---|---|
| 3 weeks | | | |
| GABAergic | 3000 ± 50 | 28 ± 8 | 33 ± 3/<1 |
| Cholinergic | 3000 ± 50 | 20 ± 5 | 0/49 ± 5 |
| 2 months | | | |
| GABAergic | 3000 ± 50 | 30 ± 7 | 25 ± 4/<1 |
| Cholinergic | 3000 ± 50 | 15 ± 3 | 0/38 ± 4 |

The data clearly demonstrate that a high percentage of GABAergic and cholinergic neurons survive 3 weeks and 2 months after surgery when transplanted 3 days after initiation of differentiation in vitro.

Example 6

A patient suffering from a spinal cord injury is treated by transplantation of differentiated CNS stem cells. CNS stem cells are collected and cultured in vitro. The cells are treated to stimulate proliferation, followed by treatment to induce differentiation into one or more specific cell types. Differentiated cells are then transplanted into the injured area of the spinal cord.

Preparation of Transplanted Cells

Autologous neuronal stem cells isolated from the patients own central nervous system are used in the transplantation process. Alternatively, embryonic or adult CNS stem from other sources, such as a donor or from existing cell lines, such as those maintained at Cedars-Sinai Medical Center, are used.

Autologous Adult Stem Cells

Small fragment of brain tissue (ependymal lining) are obtained during brain biopsy procedure by standard methods.

Surgically removed human brain tissue is placed into ice-cold DMEM/F-12 containing penicillin-streptomycin, for further dissection. The tissue is cut into small pieces (0.5-1 mm$^3$) and transferred into trypsin solution (0.02 mg/ml in Verseen (GIBCO) and incubated at 37° C. for 10-20 minutes. After incubation, trypsin inhibitor mixture (Clonetics) is added and the tissue is triturated mechanically with a Pasteur pipette. The cell suspension is centrifuged at 400 rpm for 5 minutes, the pellet is washed once with DMEM/F-12 and cells are plated at a density of 5000-10,000 viable cells/ml in 6-well Nunc tissue-culture dishes in media. The media comprises MDME/F-12 (1:1) with Hepes buffer, glucose, sodium bicarbonate, and glutamine and is supplemented with B27 supplement (GIBCO), basic fibroblast growth factor (bFGF) (20 ng/ml), leukemia inhibitory factor (LIF) (20 ng/ml) and optionally epidermal growth factor EGF (20 ng/ml).

Cell Culture

Similarly, adult or embryonic CNS stem cells from donors are grown in F12/DMEM serum free medium (GIBCO) supplemented with B27 growth supplement (GIBCO), 20 ng/ml of human recombinant LIF, bFGF (both from Pepro-Tech, Inc.) and optionally EGF (20 ng/ml). Cells are grown as a neurospheres. The media is changed every third day and neurospheres are dissociated by mechanical trituration after every 10-12 days.

Established Cell Lines from Our Tissue Bank

Embryonic and adult CNS stem cells are also available from cell banks. These CNS progenitor cells are also grown in F12/DMEM serum free medium (GIBCO) supplemented with B27 growth supplement (GIBCO), 20 ng/ml of human recombinant LIF, bFGF and optionally EGF.

To generate bulk cultures for transplantation, CNS stem cells are be passaged at high density ($10^4$-$5\times10^4$ cells/cm$^2$) every 10-12 days.

Induction of Stem Cells to Differentiate into Different Types of Excitatory and Inhibitory Neurons CNS stem cells are plated onto poly-ornithine coated tissue culture dishes in F12/DMEM serum free medium (GIBCO) supplemented with B27 growth supplement (GIBCO) and $10^{-6}$ M all-trans retinoic acid. The media may optionally also comprise one or more additional components selected from the group consisting of dBcAMP (1 mM), FGF8 (20 ng/ml) and GDNF (20 ng/ml). Cells are cultured for 3 days, after which individual treatments may be done to differentiate the cells into cholinergic, GABAergic, glutamatergic, and/or glycinergic neurons, as discussed below. Before plating cells are dissociated into smaller aggregates (50-200 cells) by mechanical trituration in growth media.

Cholinergic differentiation—cells are cultured in media containing IL-6 (20 ng/ml), NT-3 (200 ng/ml), and antisense thiomodified oligonucleotides (5 µM) blocking expression of helix-loop-helix transcriptional regulators Id1 and Id2.

GABAergic differentiation—cells are cultured in media containing brain derived neurotrophic factor (BDNF, 20 ng/ml), and antisense thiomodified oligonucleotides (5 µM) blocking expression of HE1 negative regulator of neurogenic genes.

Glutamatergic differentiation—cells are cultured in media containing 1 mM dibutyryl cyclic AMP and BDNF (20 ng/ml).

Glycinergic differentiation—cells are cultured in media containing 1 mM dibutyryl cyclic AMP and neurotrophin 3 (NT-3, 20 ng/ml).

Differentiation is evaluated by immunological staining using antibodies against choline acetyl transferase (cholinergic neurons), glutamic acid decarboxylase (GABAergic), glutamate (glutamatergic), and glycine (glycinergic).

Collection of Stem Cells for Transplantation

Cells are differentiated for 3 days, then collected by mild trypsinization (0.01% trypsin in Verseen, 5 minute at room temperature), washed twice with F12/DMEM medium, resuspended in Dulbecco modified phosphate balanced salt solution (GIBCO) and transplanted into the patient's spinal cord.

Example 7

Treatment of Mammals Suffering Striatal Damage by Transplantation of Differentiated Neuronal Stem Cells Differentiated human neural stem cells were transplanted into control and 6-OHDA lesioned rat striatum. Rotation response to amphetamine was analyzed.

Three independent cell isolates of stem cells, H3, H4 and C1 were used. The three isolates have similar characteristics, but differ in their potential to develop into dopaminergic neurons. Clones H3 and C1 achieve a high level of dopaminergic differentiation and survival after transplantation while clone H4 does not differentiate well into dopamine producing cells. Behavioral recovery was observed in animals transplanted with cells from clones H3 and C1, but no recovery was seen in H4 transplanted animals.

Table 7 summarizes the results of behavioral recovery of 6-OHDA lesioned animals. Sixty days after transplantation rotation scores had improved in 5 animals transplanted with cell clones H3 and C1. compared to pre-transplantation scores, rotation scores for these five animals were reduced 78% on average (from 50 to 95). Animals transplanted with clone H4 and control animals showed no behavioral improvement. Immunohistochemical analyses using antibodies against TH showed presence of TH-positive cells in the striatum of transplanted animals. The number of TH-positive cells was significantly higher in animals transplanted with clones H3 and C1 compared to H4. Immunohistochemical data support the finding that behavioral recovery is related to the presence of dopamine producing cells.

Human CNS stem cells were treated with 10-6 M all-trans retinoic acid (RA), 1 mM dibutyryl cyclic AMP (dBcAMP), FGF8 (20 ng/ml) and GDNF (20 ng/ml) for 3 days and transplanted into lesioned rat brain. Three different human CNS stem cell isolates H3, H4 and C1 were used. Results are in Table 7.

TABLE 7

Behavioral recovery of 6-OHDA lesioned animals after transplantation of stem cell-derived dopamine producing cells.

| | | change in rotational behavior | | |
|---|---|---|---|---|
| Clone | animal | 20 days | 40 days | 60 days |
| H3 | 1 | −40 | −45 | −50 |
|  | 2 | −10 | −12 | −12 |
|  | 3 | −60 | −80 | −95 |
|  | 4 | −20 | −60 | −90 |
| C1 | 1 | −5 | −5 | −10 |
|  | 2 | −50 | −65 | −75 |
|  | 3 | −45 | −70 | −80 |
|  | 4 | 0 | −5 | −5 |
| H4 | 1 | −5 | −5 | −10 |
|  | 2 | 0 | +5 | +20 |

TABLE 7-continued

Behavioral recovery of 6-OHDA lesioned animals after
transplantation of stem cell-derived dopamine producing cells.

| Clone | animal | change in rotational behavior | | |
|---|---|---|---|---|
| | | 20 days | 40 days | 60 days |
| | 3 | −5 | −5 | −5 |
| | 4 | 0 | 0 | +20 |
| Control | 1 | −5 | −10 | −10 |
| | 2 | 0 | +20 | +40 |
| | 3 | +20 | +45 | +60 |
| | 4 | +5 | +25 | +40 |

Animals were closely evaluated every day for abnormal clinical signs. Each animal was examined once in the morning and once in the afternoon for visual signs of motor dysfunction or other adverse signs (i.e., ataxia, paralysis, tremors, seizures, hypoactivity, etc.).

After final testing animals were sacrificed and analyzed for the survival, migration and differentiation of transplanted cells using immunohistochemical techniques. Brain sections were analyzed for general histopathology using hematoxyline/eosin staining to detect inflammation, tumor formation, morphological defects, etc.

The number of surviving cells was analyzed using anti-human ribonucleoprotein antibody. The differentiation of transplanted cells into different cell types is analyzed using double labeling immunohistochemistry. Analyses are done at different distances from the site of transplantation (1, 3, 5, 7, 10, 15, 20 mm from the transplant) to evaluate migration of transplanted cells.

Methods

Cells

Human CNS stem cells were grown in F12/DMEM serum free media (GIBCO) supplemented with B27 growth supplement (GIBCO), 20 ng/ml of human recombinant bGFG, LIF and EGF (all from PeproTech, Inc.). CNS stem cells were grown as neurospheres in 25 cm$^2$ Falcon tissue culture flasks. The media was changed every second day and spheres were dissociated by mechanical trituration after every 12-15 days.

For differentiation, cells were plated onto poly-ornithine coated tissue culture dishes in F12/DMEM serum free medium (GIBCO) supplemented with B27 growth supplement (GIBCO), $10^{-6}$ M all-trans retinoic acid, 1 mM dibutyryl cyclic AMP, FGF9 (20 ng/ml), and GDNF (20 ng/ml) and cultured 3 days. Prior to plating, cells were dissociated into smaller aggregates (50-200 cells) by mechanical trituration in growth media.

Prior to transplantation, cells were differentiated for 3 days, then collected by mild trypsinization (0.01% trypsin in Verseen, 5 minutes at room temperature), washed twice with F12/DMEM medium, resuspended in Dulbecco-modified phosphate-balanced salt solution (D-PBS, GIBCO), washed twice with D-PBS and resuspended in a small volume of D-PBS. 100,000 ocells were collected for each transplantation.

Lesion and Transplantation

Stereotactic surgery was performed under deep ketamine xylazine anesthesia. The immune system was suppressed by intramuscular injection of cyclosporin every second day. Animals were lesioned by unilateral injection of 6-hydroxydopamine (6-OHDA) at two sites along the medial forebrain bundle. Each injection contained 16 μg of 6-OHDA-HBr in 3 μl of ascorbic acid (0.2 mg/ml) in 0.9% saline. Injected animals were analyzed for amphetamine-induced rotational behavior 2 and 3 weeks before transplantation. 5 mg of d-amphetamine sulfate per kg of body weight was injected i.p. Only animals with pre-transplantation scores of over 8 rotations per minute were included in the study. Unilaterally lesioned animals received 3 μl of cell suspension in the striatum according to the following coordinates from bregma: Anterior=+0.9, Lateral=2.8 and Ventral −4.8, −4.2. The tooth bar was set at −2.3, and ventral coordinates are taken from dura. 100,000 cells were transplanted using a 5 μl Hamilton syringe. Animals were analyzed for amphetamine-induced rotational behavior 20, 40 and 60 days after transplantation.

Immunohistochemistry

Animals were sacrificed 60 days after transplantation, brains sectioned and immunostained. Sections were incubated after blocking with 3% BSA and 0.02% Tween 20 for 16 hours at 4° C. All primary antibodies were diluted in PBS containing 3% BSA and 0.02% Tween 20. Antibodies that were used in this study were anti-human nucleus antibodies (1:50, Chemicon) to detect human cells, antitype III β-tubulin antibodies (1:100, Chemicon) to detect neurons, anti tyrosine hydroxylase (1:100 Sigma) and dopa decarboxylase (1:200, Chemicon) antibodies to detect dopaminergic cells, anti gamma amino acid decarboxylase (GAD) antibodies to identify GABAergic neurons (1:1000, Chemicon), anti L-glutamate antibodies to detect glutamatergic neurons (1:50, Signature Immunologics), anti-glycine antibodies to detect glycinergic neurons (1:100, Signature Immunologics), anticholine acetyl transferase (CHAT) to detect cholinergic neurons (1:100 Chemicon) and anti GFAP antibodies (1:500, DAKO) to detect astrocytes. For double staining sections were incubated simultaneously with two primary and secondary antibodies. The second antibodies were goat anti-mouse FITC (1:200, Sigma) and goat anti-rabbit rhodamine (1:200, Boehringer).

Example 8

Tumorigenicity of Stem Cells

Stem cell were tested for their ability to form tumors following transplantation. Adult human neuronal stem cells were grown in F12/DMEM serum free medium (GIBCO) supplemented with B27 growth supplement (GIBCO), 20 ng/ml of human recombinant bFGF, EGF and LIF (all from PeproTech, Inc.). Stem cells were grown as neurospheres, media changed every second day and spheres dissociated by trituration every 12 to 15 days. 200,000 cells in growth media were stereotactically injected into anesthetized rat (n=14) and nude mouse (n=8) hippocampus and striatum. Animals were euthanized 5 months later adn analyzed for tumor formation. Rats were euthanized using a $CO_2$ chamber. Brains were removed and placed in 4% paraformaldehyde overnight. Serial sagittal sections were cut ona cryomicrotome at a thickness of 15 μM and every tenth section was stained with hematoxylin eosin for histological examination. Macroscopic and histological examination did not reveal any detectable neoplasm in the body or brain of transplanted animals.

Example 9

Treatment of Patients with Parkinson's Disease

Cells are extracted from the central nervous system of a Parkinson's patient using standard procedures and propagated in a first mixture of growth factors. A preferred first mixture comprises F12/DMEM serum free medium (e.g., GIBCO) supplemented with B27 growth supplement (e.g., GIBCO), 20 ng/ml each of human recombinant bFGF, LIF and EGF (PEPROTECH, INC.). CNS stem cells are grown as neurospheres, preferably in 25 cm² or 75 cm² FLACON tissue culture flasks. The media is changed about every second day and spheres are dissociated by mechanical trituration when necessary, preferably every 12-15 days.

When sufficient quantities of cells are available for transplantation, cells are caused to differentiate. Cells are plated onto poly-ornithine coated tissue culture dishes in F12/DMEM serum free medium (e.g., GIBCO) supplemented with a second composition. The second composition preferably comprises B27 growth supplement (GIBCO), $10^{-6}$ M all-trans retinoic acid, 1 mM dibutyryl cyclic AMP, FGF8 (20 ng/ml), and GDNF (20 ng/ml). Cells are preferably cultured about 3 days prior to transplantation. Before plating, cells are dissociated into smaller aggregates (about 50-200 cells) by mechanical trituration in growth medium.

Prior to transplantation, cells are differentiated for three days, then collected by mild trypsinization (0.01% trypsin in VERSION, 5 minutes at room temperature), washed twice in F12/DMEM medium, resuspended in Dulbecco-modified phosphate-balanced salt solution (D-PBS, GIBCO), washed twice with D-PBS and resuspended in a small volume of D-PBS. About 100,000 to about 300,000 cells are collected and used for one transplantation. The cells are reimplanted into the Parkinson's patient according to standard methods.

Example 10

Treatment of a Patient with Parkinson's Disease

Cells were extracted from a small piece of cortex from the frontal lobe of a Parkinson's patient in 1999. The sample was recovered during a craniotomy procedure. Cells were propagated in F12/DMEM serum free medium (e.g., GIBCO) supplemented with B27 growth supplement (e.g., GIBCO), 20 ng/ml human recombinant bFGF, 20 ng/ml LIF and 20 ng/ml EGF (PEPROTECH, INC.). CNS stem cells were grown as neurospheres in 25 cm² or 75 cm² FLACON tissue culture flasks. The media was changed every second day and spheres were dissociated by mechanical trituration every 12-15 days. The cells were proliferated until they numbered about six million neural stem cells and/or neurons.

To induce differentiation, cells were plated onto poly-ornithine coated tissue culture dishes in F12/DMEM serum free medium (GIBCO) supplemented with B27 growth supplement (GIBCO), $10^{-6}$ M all-trans retinoic acid (RA), 1 mM dibutyryl cyclic AMP (dBcAMP), FGF8 (20 ng/ml), and GDNF (20 ng/ml) and cultured 3 days. Before plating, cells were dissociated into smaller aggregates (about 50-200 cells) by mechanical trituration in growth medium. Prior to transplantation, cells were collected mild trypsinization (0.01% trypsin in VERSENE, 5 minutes at room temperature), washed twice in F12/DMEM medium, resuspended in Dulbecco-modified phosphate-balanced salt solution (D-PBS, GIBCO), washed twice with D-PBS and resuspended in a small volume of D-PBS.

Cells were implanted into the Parkinson's patient's left putamen in March 1999. The results of the treatment were determined to be successful. At three-month post-operatively, clinical motor scores improved by 37% and the oral dopaminergic intake decreased by 60%. F-DOPA PET studies showed a 55.1% increase in dopamine uptake in the left putamen. The patient continued to exhibit significant improvements in both clinical motor scores and increased dopamine uptake at three years post-implantation.

The procedures for removing and reimplanting the cells are known to persons skilled in the art of brain surgery.

REFERENCES CITED

Bankiewicz et al. 1991. Fetal nondopaminergic neural implants in parkinsonian primates. Journal of Neurosurgery, 74: 97-104.

Brundin et al. 1991. Intracerebral grafting of dopamine neurons: Experimental basis for clinical trials in patients with Parkinson's disease. Annals of the New York Academy of Sciences, V: 473-495.

Chalmers-Redman, R. M. E., Priestley, T., Kemp, J. A., Fine, A. 1997. In vitro propagation and inducible differentiation of multipotent progenitor cells from human fetal brain. Neurosc., 76, 1121-1128.

Chen L. et al. 1991. Cellular replacement therapy for neurologic disorders: Potential of genetically engineered sells. Journal of Cellular Biochemistry, 45; 252-257.

Davis, A. A. and Temple, S. 1994. A self-renewing multipotential stem cell in embryonic rat cerebral cortex. Nature, 372:263-266.

Diamond S. G., Markham C. H., Rand, R. W., Becker, D. P., Treciokas, L. J. 1994: Four-year follow-up of adrenal-to-brain transplants in Parkinson's disease. Archives of Neurology, 51 559-563.

Espejo, E. F., Montoro, R. J., Armengol, J. A., L6pez-Bameo, J. 1998. Cellular and functional recovery of Parkinsonian rats after intrastriatal transplantation of carotid body cell aggregates. Neuron, 20; 197-206.

Freed et al. 1989. Therapeutic effects of human fetal dopamine cells transplanted in a patient with Parkinson's disease. In S. B. Dunnet and S. R. Richards, eds. Neural Transplantation: From Molecular Basis to Clinical Application. Amsterdam: Elsevier Science Publishers, 1989.

Freed C. R., Breeze R. E., Rosenberg N. L., Schneck S. A., Kriek E., Qi J., et al. 1992. Survival of implanted fetal dopamine cells and neurologic improvement 12 to 46 months after transplantation for Parkinson's disease. New England Journal of Medicine, 327: 1549-1555.

Freeman, T and Olanow, 1991. Fetal homotransplants in the treatment of Parkinson's disease. Archives of Neurology, 48: 900-901.

Fricker, R. A., Carpenter, M. K., Winkler, C., Greco, C., Gates, M. A. and Bjorklund, A. 1999. Site-specific migration and neuronal differentiation of human neural progenitor cells after transplantation in the adult rat brain. J. Neurosci. 19: 5990-6005.

Gage and Fisher, 1991. Intracerebral grafting: A tool for the neurologist. Neuron, 6: 1-12.

Goetz et al. 1989. Multicenter study of autologous adrenal medullary transplantation to the corpus striatum in patients with advanced Parkinson's disease. New England Journal of Medicine, 320: 337-341.

Gritti et al., 1996. Multipotential stem cells from the adult mouse brain proliferate and self-renew in response to basic fibroblast growth factor. J. Neurosci. 16: 1091-1100.

Hitchcock et al. 1989. Stereotactic implantation of foetal mesencephalon (STIM): The U.K. experience. In S. B. Dunnet and S. R. Richards, eds. Neural Transplantation: From Molecular Basis to Clinical Application. Amsterdam: Elsevier Science Publishers.

Kopyov et al. 1989. Grafting of the embryonic brain tissue helps the survival of rats after severe craniocerebral trauma. Abstract, The 3rd International Symposium on Neural Transplantation, U.K., 39.

Lang, A. E., Lozano, A. M. 1998. Parkinson's disease. New England Medicine, 1130-1143.

Langston, W, et al, 1992: Core Assessment Program for Intracerebral Transplantation. Movement Disorders, vol 7: 2-13.

Leigh K., Elisevich K., Rogers K. A. 1994. Vascularization and microvascular permeability in solid versus cell suspension embryonic neural cells. Journal of Neurosurgery, 81:272-283.

Lendahl, V., Zimmerman, L. B. and McKay, R. D. G., (1990) CNS stem cells express a new class of intermediate filament protein., *Cell*, 60:585-595.

Lindvall O.: Transplants in Parkinson's disease. 1991. European Neurology, 31(Supp. 1): 17-27.

Lindvall, O., 1997. Neural transplantation: a hope for patients with Parkinson's disease. NeuroReport, 8, iii-x.

Lois, C., Alvarez-Buylla, A. 1993. Proliferating subventricular zone cells in the adult mammalian forebrain can differentiate into neurons and glia. Proc. Natl. Acad. Sci. USA, 90:2074-2077.

Markham C. M., Rand R. W., Jacques D. B., Diamond S. G., Kopyov O. V., Snow B. 1994. Transplantation of fetal mesencephalic tissue in Parkinson's patients. Stereotactic and Functional Neurosurgery, Madrazo I., Drucker-Colin R., Diaz V., Martinez-Mata J., Torres C., Becerril J. J. 1987. Open microsurgical autograft of adrenal medulla to the right caudate nucleus in two patients with intractable Parkinson's disease. New England Journal of Medicine, 316:831-834.

Nyberg et al., 1987. Dopaminergic deficiency is more pronounced in putamen than in nucleus caudatus in Parkinson's disease. Neurochem. Pathos., 1: 193-202.

Olanow, C. W., Kordower, J. H., Freeman, T. B. 1996. Foetal nigral transplantation as a therapy for Parkinsons disease. Trends NeuTosci. 19: 102-109.

Palm, K, Salin-Nordstrom, T, Levesque, M F and Neuman T: Fetal and adult human CNS stem cells have similar molecular characteristics and developmental potential Brain Res Mol Brain Res. 2000 May 31; 78(1-2):192-5.

Palmer, T. O., Takahashi, J., Gage, F. H. 1997. The adult rat hippocampus contains primordial neural stem cells. Mol. Cell. Neurosci. 8: 389-404.

Reynolds, B. A., Weiss, S. 1992. Generation of neurons and astrocytes from isolated cells of the adult mammalian central nervous system. Science, 255: 1707-1710.

Rosenthal, A. 1998. Auto transplants for Parkinson's disease? Neuron, 20:169-172.

Sakakibara, 5., Imai, T., Hamaguchi, K, Okabe, M., Aruga, J., Nakajima, K., Yasutomi, D., Nagata, T., Kurihara, Y., Uesugi, 5., Miyata, T., Ogawa, M., Mikoshiba, K. and Okaino, H. 1996 Mouse-Musashi-1, a neural RNA-binding protein highly enriched in the mammalian CNS stem cell., *Dev. Bioi.*, 176:230-242.

Schierle, G. S., Hansson, O., Leist, M., Nicotera, P., Widner, H., Brundin, P. 1999. Caspase inhibition reduces apoptosis and increases survival of nigral transplants. Nat Med, 5: 97-100.

Spencer D. O., Robbins R. J., Naftolin F., Marek K. L., Vollmer T., Leranth C., et al. 1992. Unilateral transplantation of human fetal mesencephalic tissue into the caudate nucleus of patients with Parkinson's disease. New England Journal of Medicine, 327: 1541-1548.

Sinclair, S. R., Svendsen, C. N., Torres, E. M., Fawsett, I. W., Dunnett, S. B. 1996. The effects of glial cell line-derived neurotrophic factor (GDNF) on embryonic nigra I grafts. NeuroReport, 7:2547-2552.

Suhonen, J. O., Peterson, D. A., Ray, J., Gage, F. H. 1996. Differentiation of adult hippocampus-derived progenitors into olfactory neurons in vivo. Nature, 383:624-627.

Svendsen, C. N., Clarke, D.]., Rosser, A. E., Dunnett, S. B. 1996. Survival and differentiation of rat and human epidermal growth factor-responsive precursor cells following grafting into the lesioned adult central nervous system. Exp. Neurol., 137, 376-388.

Vescovi, A. L., Parati, E. A., Gritti, A., Poulin, P., Ferrario, M., Wanke, E., Frolichsthal-Schoeller, P., Cova, L., Arcellana-Panililio, M., Colombo, A. and Galli, R. 1999. Isolation and cloning of multipotential stem cells from the embryonic human CNS and establishment of transplantable human neural stem cell lines by epigenetic stimulation. Exp. Neurol. 156, 71-83.

Vescovi, A. L., Daadi, M., Asham, R., Reynolds, B. A. 1997. Continuous generation of human catecholaminergic neurons by embryonic CNS stem cells. Vol. 23 (I). In 27th Meeting Soc. Neurosci.: New Orleans, La., 25-30 October: Abs. 131.6, pp 319.

Zawada, W. M., Zastrow, D.]., Clarkson, E. D., Adams, F. S., Bell, K. P., Freed, C. R. 1998. Growth factors improve immediate survival of embryonic dopamine neurons after transplantation into rats. Brain Res., 786 (1-2): 96-103.

What is claimed is:

1. A method of administering GABAergic neurons into a patient suffering from Parkinson's disease, comprising:
   (a) obtaining central nervous system (CNS) stem cells;
   (b) initiating differentiation of the CNS stem cells into differentiated cells comprising GABAergic neurons by culturing them in vitro in differentiation medium comprising fibroblast growth factor 8 (FGF8), glial cell line derived neurotrophic factor (GDNF), all-trans retinoic acid (RA) and dibutyryl cyclic AMP (dBcAMP);
   (c) analyzing the development of GABAergic neurons in the differentiated cells; and
   (d) transplanting, 2-4 days after the initiation of differentiation, the CNS stem cells including GABAergic neurons into the central nervous system of the patient, wherein the transplanting is performed before the cells are fully differentiated.

2. The method of claim 1 wherein the CNS stem cells are human.

3. The method of claim 1 wherein the CNS stem cells are obtained from the patient.

4. The method of claim 1 wherein the CNS stem cells are obtained from an unrelated donor.

5. The method of claim 1 wherein obtaining the CNS stem cells comprises surgically removing a sample of central nervous system tissue from a patient.

6. The method of claim 5 wherein a sample of cortex is removed from the frontal lobe of a patient.

7. The method of claim 1 wherein the differentiation medium comprises $10^{-6}$ M RA, 1 mM dBcAMP, 20 ng/ml FGF8 and 20 ng/ml GDNF.

8. The method of claim 1 additionally comprising proliferating the CNS stem cells by culturing them in vitro in proliferation medium comprising basic fibroblast growth factor (bFGF), leukemia inhibitory factor (LIF) and epidermal grow factor (EGF) prior to differentiating the CNS stem cells.

9. The method of claim 8 wherein the proliferation medium comprises ng/ml bFGF, 20 ng/ml LIF and 20 ng/ml EGF.

10. The method of claim 1 wherein the CNS stem cells are differentiated for three days prior to transplantation.

11. The method of claim 1 wherein the differentiated CNS stem cells are transplanted into the caudate nucleus in the patient's brain.

12. The method of claim 1 wherein the differentiated CNS stem cells are transplanted into the putamen in the patient's brain.

13. The method of claim 12, wherein the differentiated CNS stem cells are transplanted into the putamen and the caudate nucleus in the patient's brain.

14. The method of claim 1, wherein the differentiated CNS stem cells are transplanted about 3 days after initiation of differentiation.

15. A method of alleviating the locomotor symptoms of Parkinson's Disease in a patient suffering from Parkinson's disease comprising:
  (a) obtaining central nervous system (CNS) stem cells from the patient;
  (b) proliferating the CNS stem cells by culturing the cells in a first medium comprising bFGF, LIF and EGF;
  (c) initiating differentiation of the CNS stem cells into a population of differentiated cells comprising GABAergic neurons by culturing the cells in a second medium comprising RA, dBcAMP, GDNF and FGF8;
  (d) analyzing the development of GABAergic neurons in the differentiated cells; and
  (e) transplanting, 2-4 days after the initiation of differentiation, the cells including GABAergic neurons into the patient's brain, wherein the transplanting is performed before the cells are fully differentiated.

16. The method of claim 15 wherein the CNS stem cells are obtained from the cortex of the patient during craniotomy.

17. The method of claim 15 wherein the first medium comprises about 0.2 to about 200 ng/ml each of bFGF, LIF and EGF.

18. The method of claim 17 wherein the first medium comprises about 20 ng/ml each of bFGF, LIF and EGF.

19. The method of claim 15 wherein the second medium comprises about $10^{-8}$ to about $10^{-4}$ M RA, about 0.01 to about 3 mM dBcAMP, about 0.02 to about 200 ng/ml FGF8, and about 0.02 to about 200 ng/ml GDNF.

20. The method of claim 19 wherein the second medium comprises $10^{-6}$ M RA, 1 mM dBcAMP, 20 ng/ml FGF8 and 20 ng/ml GDNF.

21. The method of claim 15 wherein the differentiated cells are transplanted into the caudate nucleus in the patient's brain.

22. The method of claim 15 wherein the differentiated cells are transplanted into the putamen in the patient's brain.

23. The method of claim 15 wherein the cells are differentiated for three days prior to transplantation.

24. The method of claim 15 wherein the patient receives from about 0.5 million to about 80 million differentiated cells.

25. The method of claim 24 wherein the patient receives from about 4 million to about 10 million differentiated cells.

* * * * *

UNITED STATES PATENT AND TRADEMARK OFFICE
CERTIFICATE OF CORRECTION

PATENT NO. : 7,632,680 B2 Page 1 of 1
APPLICATION NO. : 10/216677
DATED : December 15, 2009
INVENTOR(S) : Neuman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 929 days.

Signed and Sealed this

Second Day of November, 2010

David J. Kappos
*Director of the United States Patent and Trademark Office*